United States Patent [19]

Shewmaker et al.

[11] Patent Number: 5,349,123
[45] Date of Patent: Sep. 20, 1994

[54] GLYCOGEN BIOSYNTHETIC ENZYMES IN PLANTS

[75] Inventors: Christine K. Shewmaker, Woodland; David M. Stalker, Davis, both of Calif.

[73] Assignee: Calgene, Inc., Davis, Calif.

[21] Appl. No.: 735,065

[22] Filed: Jul. 24, 1991

Related U.S. Application Data

[63] Continuation-in-part of Ser. No. 632,383, Dec. 21, 1990, abandoned, and a continuation-in-part of Ser. No. 731,226, Jul. 16, 1991, abandoned.

[51] Int. Cl.$^5$ .................... A01H 1/04; C12N 15/00; C07H 21/04; C12P 21/04
[52] U.S. Cl. .................... 800/205; 800/DIG. 41; 800/DIG. 52; 800/DIG. 55; 800/DIG. 56; 800/DIG. 57; 435/69.1; 435/69.8; 435/70.1; 435/172.3; 435/240.4; 536/23.2; 536/23.7; 536/24.1; 536/23.4
[58] Field of Search .................... 435/69.1, 69.8, 70.1, 435/172.3, 240.4, 320.1, 183; 536/27, 23.2, 23.7, 24.1, 23.4; 800/205, DIG. 42, DIG. 52, DIG. 55, DIG. 56, DIG. 57

[56] References Cited

U.S. PATENT DOCUMENTS 4,696,674 9/1987 Cipar .................... 800/200

OTHER PUBLICATIONS

Preiss, "Bacterial Glycogen Synthesis and Its Regulation," Ann. Rev. Microbiol. (1984) 38:419–458.

Kumar et al., "Biosynthesis of Bacterial Glycogen: Primary Structure of *Escherichia coli* ADP-glucose:α-1, 4-glucan, 4-glucosyltransferase as Deduced from the Nucleotide Sequence of the glgA Gene," J. Biol. Chem. (1986) 261:16256–16259.

Leung et al., "Cloning and Expression of the *Escherichia coli* glgC Gene from a Mutant Containing an ADPglucose Pyrophosphorylase with Altered Allosteric Properties," J. Bacteriol. (1986) 167:82–88.

Leung and Preiss, "Biosynthesis of Bacterial Glycogen: Primary Structure of *Salmonella typhimurium* ADP-glucose Synthesis as Deduced from the Nucleotide Sequence of the glgC Gene," J. Bacteriol. (1987) 169:4355–4360.

Lee et al., "Amino Acid Sequence of an *Escherichia coli* ADPglucose Synthetase Allosteric Mutant as Deduced from the DNA sequence of the glgC Gene," Nucleic Acids Res. (1987) 15:10603.

Smith, "Major Differneces in Isoforms of Starch-Branching Enzyme Between Developing Embryos of Round- and Wrinkled-Seeded Peas (*Pisum sativum* L.)," Planta (1988) 175:270–279.

Browner et al., "Human Muscle Glycogen Synthase cDNA Sequence: A Negatively Charged Protein with an Asymmetric Charge Distribution," Proc. Nat. Acad. Sci. (1989) 86:1443–1447.

Bai et al., "The Primary Structure of Rat Liver Glycogen Synthase Deduced by cDNA Cloning: Absense of Phosphorylation Sites 1a and 1b," J. Biol. Chem. (1990) 265:7843–7848.

Anderson et al., "The Encoded Primary Sequence of a Rice Seed ADP-glucose Pyrophosphorylase Subunit and Its Homology to the Bacterial Enzyme," J. Biol. Chem. (1989) 264:12238–12242.

Anderson et al., "Enhancing Carbon Flow Into Starch: The Role of ADP-glucose Pyrophosphorylase," (1990) *The Molecular and Cellular Biology of the Potato*, eds. M.

(List continued on next page.)

*Primary Examiner*—David T. Fox

[57] ABSTRACT

This invention relates to glycogen biosynthesis enzymes in plants. In particular, this invention is directed to plant cells having a DNA sequence encoding a glycogen biosynthesis enzyme integrated in its genome as the result of genetic engineering. Cells containing a DNA or RNA (mRNA) sequence encoding the enzyme as well as cells containing the enzyme are also provided. Plants and, more particularly, plant parts may also be obtained which contain glycogen biosynthesis enzyme sequences and/or containing such glycogen biosynthesis enzymes.

16 Claims, 13 Drawing Sheets

OTHER PUBLICATIONS

E. Vayda and W. D. Park, Chapter 12, pp. 159–180.
Okita et al. 1981, J. Biol. Chem. 256(13):6944–6952.
Olive et al. 1989, Plant Mol. Biol. 12(5):525–538.
Sowokinos et al. 1985, Plant Physiol. 78:489–494.
Sengupta-Gopalan et al. 1985, Proc. Natl. Acad. Sci. USA 82:3320–3324.
Hovenkamp-Hermelink et al. 1987, Theor. Appl. Genet. 75:217–221.
Kumar et al. 1986, J. Biol. Chem. 261(34):16256–16259.
Twell et al. 1987, Plant Mol. Biol. 9:365–375.
Schreier et al. 1985, EMBO J. 4(2):25–32.
Anderson et al. 1990, pp. 159–180 In: Mol. Cell. Biol. Potato, Ch. 12, Vayda et al., eds.
Anderson et al. 1989, J. Biol. Chem. 264:12238–12242.
Muller-Rober, et al., "One of Two Different ADP—Glucose Pyrophosphorylase Genes From Potato Responds Strongly To Elevated Levels Of Sucrose," *Mol. Gen. Genet.* (1990) 224:136–146.
Visser, et al., "Molecular Cloning and Partial Characterization Of the Gene For Granule-Bound Starch Synthase From a Wildtype and an Amylose-Free Potato (*Solanum tubersoum L.*)," Plant Science (1989) 64:185–192.
Visser, et al., "Inhibition of the Expression of the Gene for Granule-Bound Starch Synthase in Potato by Antisense Constructs," *Mol Gen Genet* (1991) 225:289–296.
Baecker, et al., "Biosynthesis of Bacterial Glycogen" *J. of Biological Chem.* (1983) 258(8):5084–5088**.
van der Leij, et al., "Expression of The Gene Encoding Granule Bound Starch Synthase After Introduction In An Amylose-Free and a Wild-Type Potato (*Solanum tuberosum*)," (1990) Int'l Congress On Plant Tissue and Cell Culture, Amsterdam Jun. 24–29, Abstract A5-28.
Visser, et al., "Manipulation of Starch in Potatoes By New Mutants and Antisense RNA," (1990) J. Cell. Biochem. Suppl. vol. 14E, p. 271, Abstract R028.

GLGA-40

| | | | | | |
|---|---|---|---|---|---|
| GATCTAACAG | GAGCGATAAT | GCAGGTTTTA | CATGTATGTT | CAGAGATGTT | CCCGCTGCTT | 60
| AAAACCGGCG | GTCTGGCTGA | TGTTATTGGG | GCATTACCCG | CAGCACAAAT | CGCAGACGGC | 120
| GTTGACGCTC | GCGTACTGTT | GCCTGCATTT | CCCGATATTC | GCCGTGGCGT | GACCGATGCG | 180
| CAGGTAGTAT | CCCGTCGTGA | TACCTTCGCC | GGACATATCA | CGCTGTTGTT | CGGTCATTAC | 240
| AACGGGGTTG | GCATTTACCT | GATTGACGCG | CCGCATCTCT | ATGATCGTCC | GGGAAGCCCG | 300
| TATCACGATA | CCAACTTATT | TGCCTATACC | GACAACGTAT | TGCGTTTTGC | GCTGCTGGGG | 360
| TGGGTTGGGG | CAGAAATGGC | CAGCGGGCTT | GACCCATTCT | GGGCGTCCTGA | TGTGGTGCAT | 420
| GCGCACGACT | GGCATGCAGG | CCTTGCGCCT | GCGTATCTGG | CGGCGGCCGG | GCGTCCGGCG | 480
| AAGTCGGTGT | TTACTGGGCA | CAACCTGGCC | TATCAAGGCA | TGTTTTATGC | ACATCACATG | 540

FIG. 1A

| | | | | |
|---|---|---|---|---|
| AATGACATCC | AATTGCCATG | GTCATTCTTT | AATATTCATG | GGCTGGAATT CAACGGACAA 600 |
| ATCTCTTTCC | TGAAGGCCGG | TCTGTACTAT | GCCGATCACA | TTACGGCGGT CAGTCCAACC 660 |
| TACGCTCGCG | AGATCACCGA | ACCGCAGTTT | GCCTACGGTA | TGGAAGGTCT GTTGCAACAG 720 |
| CGTCACCGTG | AAGGGCGTCT | TTCCGGGCGTA | CTGAACGGGCG | TGGACGAGAA AATCTGGAGT 780 |
| CCAGAGACGG | ACTTACTGTT | GGCCTCGCGT | TACACCCCGCG | ATACGTTGGA AGATAAAGCG 840 |
| GAAAATAAGC | GCCAGTTACA | AATCGCAATG | GGGCTTAAGG | TTGACGATAA AGTGCCGCTT 900 |
| TTTGCAGTGG | TGAGCCGTCT | GACCAGCCAG | AAAGGTCTCG | ACCTGGTGCT GGAAGCCTTA 960 |
| CCGGGTCTTC | TGGAGCAGGG | CGGCTACTCG | GCGCTGGGCGA | TCCGGTGCTG 1020 |
| CAGGAAGGTT | TCCTTGCGGC | GGCAGTGGAA | TACCCCGGTC | AGGTGGGCGT TCAGATTGGC 1080 |

FIG. 1B

```
TATCACGAAG CATTTTCGCA TCGCATTATG GGCGGGCGCGG ACGTCATTCT GGTGCCCAGC 1140
CGTTTTGAAC CGTGCGGCTT AACGCAACTT TATGGATTGA AGTACGGTAC GCTGCCGTTA 1200
GTGCGGGCGCA CCGGTGGGCT TGCTGATACG GTTTCTGACT GTTCTCTTGA GAACCTTGCA 1260
GATGGCGTCG CCAGTGGGTT TGTCTTTGAA GATAGTAATG CCTGGTCGCT GTTACGGGCT 1320
ATTCGACGTG CTTTTGTACT GTGGTCCCGT CCTTCACTGT GGCGGTTTGT GCAACGTCAG 1380
GCTATGGCAA TGGATTTTAG CTGGCAGGTC GCGGCGAAGT CGTACCGTGA GCTTTACTAT 1440
CGCTCGAAAT AGTTTTCAGT CGAC                                      1464
```

FIG. 1C

GLGA-40

MET Gln Val Leu His Val Cys Ser Glu MET Phe Pro Leu Leu Lys Thr
1                           5                              10                             15

Gly Gly Leu Ala Asp Val Ile Gly Ala Leu Pro Ala Ala Gln Ile Ala
                  20                             25                             30

Asp Gly Val Asp Ala Arg Val Leu Leu Pro Ala Phe Pro Asp Ile Arg
                  35                             40                             45

Arg Gly Val Thr Asp Ala Gln Val Val Ser Arg Arg Asp Thr Phe Ala
                  50                             55                             60

Gly His Ile Thr Leu Leu Phe Gly His Tyr Asn Gly Val Gly Ile Tyr
65                             70                             75                             80

Leu Ile Asp Ala Pro His Leu Tyr Asp Arg Pro Gly Ser Pro Tyr His
                  85                             90                             95

Asp Thr Asn Leu Phe Ala Tyr Thr Asp Asn Val Leu Arg Phe Ala Leu
100                            105                            110

FIG. 2A

Leu Gly Trp Val Gly Ala Glu MET Ala Ser Gly Leu Asp Pro Phe Trp
115                 120                 125

Arg Pro Asp Val Val His Ala His Asp Trp His Ala Gly Leu Ala Pro
130                 135                 140

Ala Tyr Leu Ala Ala Arg Gly Arg Pro Ala Lys Ser Val Phe Thr Gly
145                 150                 155                 160

His Asn Leu Ala Tyr Gln Gly MET Phe Tyr Ala His His MET Asn Asp
165                 170                 175

Ile Gln Leu Pro Trp Ser Phe Phe Asn Ile His Gly Leu Glu Phe Asn
180                 185                 190

Gly Gln Ile Ser Phe Leu Lys Ala Gly Leu Tyr Tyr Ala Asp His Ile
195                 200                 205

Thr Ala Val Ser Pro Thr Tyr Ala Arg Glu Ile Thr Glu Pro Gln Phe
210                 215                 220

FIG. 2B

```
Ala Tyr Gly MET Glu Gly Leu Gln Gln Arg His Arg Glu Gly Arg
225                 230                 235                 240

Leu Ser Gly Val Leu Asn Gly Val Asp Glu Lys Ile Trp Ser Pro Glu
        245                 250                 255

Thr Asp Leu Leu Leu Ala Ser Arg Tyr Thr Arg Asp Thr Leu Glu Asp
            260                 265                 270

Lys Ala Glu Asn Lys Arg Gln Leu Gln Ile Ala MET Gly Leu Lys Val
        275                 280                 285

Asp Asp Lys Val Pro Leu Phe Ala Val Val Ser Arg Leu Thr Ser Gln
    290                 295                 300

Lys Gly Leu Asp Leu Val Leu Glu Ala Leu Pro Gly Leu Leu Glu Gln
305                 310                 315                 320

Gly Gly Gln Leu Ala Leu Leu Gly Ala Gly Asp Pro Val Leu Gln Glu
            325                 330                 335
```

FIG. 2C

Gly Phe Leu Ala Ala Ala Ala Glu Tyr Pro Gly Gln Val Gly Val Gln
340                                345                         350

Ile Gly Tyr His Glu Ala Phe Ser His Arg Ile MET Gly Gly Ala Asp
355                                360                         365

Val Ile Leu Val Pro Ser Arg Phe Glu Pro Cys Gly Leu Thr Gln Leu
370                                375                         380

Tyr Gly Leu Lys Tyr Gly Thr Leu Pro Leu Val Arg Arg Thr Gly Gly
385                                390                         395                400

Leu Ala Asp Thr Val Ser Asp Cys Ser Leu Glu Asn Leu Ala Asp Gly
                405                                410                         415

Val Ala Ser Gly Phe Val Phe Glu Asp Ser Asn Ala Trp Ser Leu Leu
            420                                425                         430

Arg Ala Ile Arg Arg Ala Phe Val Leu Trp Ser Arg Pro Ser Leu Trp
        435                                440                         445

FIG. 2D

```
Arg Phe Val Gln Arg Gln Ala MET Ala MET Asp Phe Ser Trp Gln Val
450                 455                 460

Ala Ala Lys Ser Tyr Arg Glu Leu Tyr Tyr Arg Ser Lys
465                 470                 475
```

FIG. 2E

```
GATCTAGGAG CGATA ATG GTT AGT TTA GAG AAG AAC GAT CAC TTA ATG         48
                MET Val Ser Leu Glu Lys Asn Asp His Leu MET
                 1                   5                  10

TTG GCG CGC CAG CTG CCA TTG AAA TCT GTT GCC CTG ATA CTG GCG GGA      96
Leu Ala Arg Gln Leu Pro Leu Lys Ser Val Ala Leu Ile Leu Ala Gly
            15                  20                  25

GGA CGT GGT ACC CGC CTG AAG GAT TTA ACC AAT AAG CGA GCA AAA CCG     144
Gly Arg Gly Thr Arg Leu Lys Asp Leu Thr Asn Lys Arg Ala Lys Pro
        30                  35                  40

GCC GTA CAC TTC GGC GGT AAG TTC CGC ATT ATC GAC TTT GCG CTG TCT     192
Ala Val His Phe Gly Gly Lys Phe Arg Ile Ile Asp Phe Ala Leu Ser
    45                  50                  55

AAC TGC ATC AAC TCC GGG ATC CGT ATG CGT ATG GGC GTG ATC ACC CAG TAC 240
Asn Cys Ile Asn Ser Gly Ile Arg Met Arg Met Gly Val Ile Thr Gln Tyr
60                  65                  70                  75

CAG TCC CAC ACT CTG GTG CAG CAC ATT CAG CGC GGC TGG TCA TTC TTC     288
Gln Ser His Thr Leu Val Gln His Ile Gln Arg Gly Trp Ser Phe Phe
            80                  85                  90
```

FIG. 3A

| AAT Asn | GAA Glu | ATG MET | AAC Asn | GAG Glu | TTT Phe | GTC Val | GAT Asp | CTG Leu | CTG Leu | CCA Pro | GCA Ala | CAG Gln | CAG Gln | AGA Arg | 336 |
|---|---|---|---|---|---|---|---|---|---|---|---|---|---|---|---|
| | Glu 95 | | | | | | | 100 | | | | | 105 | | |

| ATG MET | AAA Lys | GGG Gly | GAA Glu | AAC Asn | TGG Trp | TAT Tyr | CGC Arg | GGC Gly | ACC Thr | GCA Ala | GAT Asp | GCG Ala | GTC Val | ACC Thr | CAA Gln | 384 |
|---|---|---|---|---|---|---|---|---|---|---|---|---|---|---|---|---|
| | | 110 | | | | | 115 | | | | | 120 | | | | |

| AAC Asn | CTC Leu | GAC Asp | ATT Ile | ATC Ile | CGC Arg | CGT Arg | TAT Tyr | AAA Lys | GCG Ala | GAA Glu | TAC Tyr | GTG Val | GTG Val | ATC Ile | CTG Leu | 432 |
|---|---|---|---|---|---|---|---|---|---|---|---|---|---|---|---|---|
| | | 125 | | | | | 130 | | | | | 135 | | | | |

| GCG Ala | GGC Gly | GAC Asp | CAT His | ATC Ile | TAC Tyr | AAG Lys | CAA Gln | GAC Asp | TAC Tyr | TCG Ser | CGT Arg | ATG MET | CTT Leu | ATC Ile | GAT Asp | 480 |
|---|---|---|---|---|---|---|---|---|---|---|---|---|---|---|---|---|
| | | 140 | | | | | 145 | | | | | 150 | | | | 155 |

| CAC His | GTC Val | GAA Glu | AAA Lys | GGC Gly | GCA Ala | CGT Arg | TGC Cys | ACC Thr | GTT Val | GCT Ala | TGT Cys | ATG MET | CCA Pro | GTA Val | CCG Pro | 528 |
|---|---|---|---|---|---|---|---|---|---|---|---|---|---|---|---|---|
| | | | | 160 | | | | | 165 | | | | | 170 | | |

| ATT Ile | GAA Glu | GAA Glu | GCC Ala | TCC Ser | GCA Ala | TTT Phe | GGC Gly | GTT Val | ATG MET | GCG Ala | GTT Val | GAT Asp | GAG Glu | AAC Asn | GAT Asp | 576 |
|---|---|---|---|---|---|---|---|---|---|---|---|---|---|---|---|---|
| | | | | 175 | | | | | 180 | | | | | 185 | | |

FIG. 3B

```
AAA ATT ATC GAA TTC GTT GAA AAA CCT GCT AAC CCG CCG TCA ATG CCG    624
Lys Ile Ile Glu Phe Val Glu Lys Pro Ala Asn Pro Pro Ser MET Pro
        190                 195                 200

AAC GAT CCG AGC AAA TCT CTG GCG AGT ATG GGT ATC TAC GTC TTT GAC    672
Asn Asp Pro Ser Lys Ser Leu Ala Ser MET Gly Ile Tyr Val Phe Asp
        205                 210                 215

GCC GAC TAT CTG TAT GAA CTG CTG GAA GAA GAC GAT CGC GAT GAG AAC    720
Ala Asp Tyr Leu Tyr Glu Leu Leu Glu Glu Asp Asp Arg Asp Glu Asn
        220                 225                 230                 235

TCC AGC CAC GAC TTT GGC AAA GAT TTG ATT CCC AAG ATC ACC GAA GCC    768
Ser Ser His Asp Phe Gly Lys Asp Leu Ile Pro Lys Ile Thr Glu Ala
        240                 245                 250

GGT CTG GCC TAT GCG CAC CCG TTC CCG CTC TCT TGC GTA CAA TCC GAC    816
Gly Leu Ala Tyr Ala His Pro Phe Pro Leu Ser Cys Val Gln Ser Asp
        255                 260                 265
```

FIG. 3C

```
CCG GAT GCC GAG CCG TAC TGG CGC GAT GTG GGT ACG CTG GAA GCT TAC    864
Pro Asp Ala Glu Pro Tyr Trp Arg Asp Val Gly Thr Leu Glu Ala Tyr
        270                 275                 280

TGG AAA GCG AAC CTC GAT CTG GCC TCT GTG GTG CCG GAA CTG GAT ATG    912
Trp Lys Ala Asn Leu Asp Leu Ala Ser Val Val Pro Glu Leu Asp MET
    285                 290                 295

TAC GAT CGC AAT TGG CCA ATT CGC ACC TAC AAT GAA TCA TTA CCG CCA    960
Tyr Asp Arg Asn Trp Pro Ile Arg Thr Tyr Asn Glu Ser Leu Pro Pro
300                 305                 310                 315

GCG AAA TTC GTG CAG GAT CGC TCC GGT TGT GTG ATC TCC GGT ATG ACC   1008
Ala Lys Phe Val Gln Asp Arg Ser Gly Cys Val Ile Ser Gly MET Thr
                320                 325                 330

CTT AAC TCA CTG GTT TCC GAC GGT TGT GTG ATC TCC GGT TCG GTG GTG   1056
Leu Asn Ser Leu Val Ser Asp Gly Cys Val Ile Ser Gly Ser Val Val
            335                 340                 345

CAG TCC GTT CTG TTC TCG CGC GTT AAT TCA TTC TGC GAC ATT GAT        1104
Gln Ser Val Leu Phe Ser Arg Val Asn Ser Phe Cys Asp Ile Asp
        350                 355                 360
```

FIG. 3D

```
TCC GCC GTA TTG TTA CCG GAA GTA TGG GTA GGT CGC TCG TGC CGT CTG    1152
Ser Ala Val Leu Leu Pro Glu Val Trp Val Gly Arg Ser Cys Arg Leu
365                 370                 375

CGC CGC TGC GTC ATC GAT CGT GCT TGT GTT ATT CCG GAA GGC ATG GTG    1200
Arg Arg Cys Val Ile Asp Arg Ala Cys Val Ile Pro Glu Gly MET Val
380                 385                 390                 395

ATT GGT GAA AAC GCA GAG GAA GAT GCA CGT CGT TTC TAT CGT TCA GAA    1248
Ile Gly Glu Asn Ala Glu Glu Asp Ala Arg Arg Phe Tyr Arg Ser Glu
        400                 405                 410

GAA GGC ATC GTG CTG GTA ACG CGC GAA ATG CTA CGG AAG TTA GGG CAT    1296
Glu Gly Ile Val Leu Val Thr Arg Glu MET Leu Arg Lys Leu Gly His
        415                 420                 425

AAA CAG GAG CGA TAATGCAGGG TCGAC                                   1323
Lys Gln Glu Arg
        430
```

FIG. 3E

GLYCOGEN BIOSYNTHETIC ENZYMES IN PLANTS

This application is a continuation-in-part of U.S. Ser. No. 07/632,383 filed Dec. 21, 1990, now abandoned, and a continuation-in-part of U.S. Ser. No. 07/731,226 filed on Jul. 16, 1991, now abandoned.

TECHNICAL FIELD

The present invention is directed to compositions and methods related to sequences relevant to the biosynthesis of glycogen and their use in plants.

INTRODUCTION

BACKGROUND

In the animal kingdom, as well as in some lower plants, i.e., nonvascular plants, fungi, yeast and bacteria, the primary reserve polysaccharide is glycogen. Glycogen is a polysaccharide containing linear molecules with α1, 4 glycosyl linkages and is branched via α1, 6 glycosyl linkages. Although from a linkage comparison, glycogen is analogous to starch, glycogen exhibits a different chain length and degree of polymerization. In bacteria, for example, the α1, 6 glycosyl linkages constitute only approximately 10% of the total linkages, indicating that the majority of the glycogen polymer resides as a linear glucose molecule.

In plants, i.e. vascular plants, reserve polysaccharides are stored in roots, tubers and seeds irk the form of starch. Starch, a complex polymer of glucose, consists of a mixture of linear chain and branched chain glucans known as amylose and amylopectin respectively. Starches isolated from different plants are found to have variable contents of amylose. Typically, amylose comprises from about 10-25% of plant starch, the remainder being the branched polymer amylopectin. Amylopectin contains low molecular weight chains and high molecular weight chains, with the low molecular weight chains ranging from 5-30 glucose units and the high molecular weight chains from 30-100 or more. The ratio of amylose/amylopectin and the distribution of low molecular weight to high molecular weight chains in the amylopectin fraction are known to affect the properties, such as thermal stabilization, retrogradation, and viscosity, and therefore utility of starch. The highest published low m.w./high m.w. chain ratios (on a weight basis) in amylopectin are 3.9/1 for waxy corn starch which has unique properties. Additionally, duwx, which has slightly more branch points than waxy has further unique properties.

In addition, starches from different plants or plant parts often have different properties. For example, potato starch has different properties than other starches, some of which may be due to the presence of phosphate groups. In some plant species, mutants have been identified which have altered contents of amylose and amylopectin. Mutations that affect the activity of starch-branching enzyme in peas, for example, result in seeds having less starch and a lower proportion of amylopectin. Also, mutations in the waxy locus of maize, which encodes a starch granule bound starch synthase, result in plants which produce amylopectin exclusively. Similarly, a potato mutant has been identified whose starch is amylose-free (Hovenkamp-Hermelink et al. *Theor. Appl. Genet.* (1987) 75:217-221). It has been found that varying the degree of starch branching can confer desirable physical properties; other changes in the characteristics of native starch could result in the production of polymers with new applications.

With the development of genetic engineering techniques, it is now possible to transfer genes from a variety of organism into the genome of a large number of different plant species. This process is preferable to plant breeding techniques whereby genes can only be transferred from one plant in a species to another plant in that same species or to a plant from a different, but closely related species. It would thus be desirable to develop plant varieties through genetic engineering, which have increased capacity for starch synthesis, altered amylose/amylopectin ratios, altered distribution of low to high molecular weight chains in the amylopectin fraction and also starches with novel molecular weight characteristics. In this manner, useful starches with a variety of viscosity or texture differences may be obtained.

To this end, nucleic acid sequences which encode glycogen biosynthetic enzymes are desirable for study and manipulation of the starch biosynthetic pathway. In particular, these enzymes may be expressed in plant cells using plant genetic engineering techniques and targeted to a plastid where starch synthesis occurs.

Relevant Literature

The structural genes encoding the *E. coli* glycogen biosynthetic enzymes have been cloned (Okita, et al. (1981) *J. Biol. Chem.* 256:6944-6952) and their nucleic acid sequences determined (Preiss, J. (1984) *Ann. Rev. Microbiol.* 38:419-458; Kumar et al. (1986) *J. Biol. Chem.* 261:16256-16259). Genes encoding mammalian glycogen synthases have also been cloned and their nucleic acid sequences determined (Browner, et al. *Proc. Nat. Acad. Sci.* (1989) 86:1443-1447; Bai, et al., *J. Biol Chem.* (1990) 265:7843-7848).

BRIEF DESCRIPTION OF THE DRAWINGS

FIG. 1 depicts a DNA sequence (SEQ ID NO: 1) for the *E. coli* glycogen synthase gene, glgA, generated through Polymerase Chain Reaction (PCR) from *E. coli* K-12 618.

FIG. 2 depicts the translated amino acid sequence (SEQ ID NO:2) of the PCR generated glgA gene.

FIG. 3 depicts DNA sequence (SEQ ID NO: 3) and the translated amino acid sequence of the PCR generated *E. coli* ADP-glucose pyrophosphorylase gene, glgC, from *E. coli* K-12 618.

SUMMARY OF THE INVENTION

By this invention, nucleic acid constructs comprising a glycogen biosynthetic enzyme sequence and at least one sequence endogenous to a plant are provided. As plants do not produce glycogen, these enzymes and sequences are not naturally found in a plant cell. Particularly, this invention relates to constructs comprising sequences relating to the glycogen biosynthetic enzymes, glycogen synthase and/or ADP-glucose pyrophosphorylase.

In one aspect of the invention, a sequence encoding a glycogen biosynthetic enzyme is joined to a sequence which encodes a transit peptide that provides for translocation of the glycogen biosynthetic enzyme to a plastid.

Other constructs of this invention provide sequences for transcription of glycogen biosynthetic enzyme sequences in plant cells. To this end, transcriptional initiation regions that function to regulate expression of genes in plants are considered. Of particular interest are those regulatory regions that preferentially direct expression of genes in roots, tubers, and seeds of plants or in other plant parts that synthesize reserve starch. In addition, constructs may contain sequences encoding a marker enzyme for selection of transformed cells.

Expression constructs which comprise sequences which provide for transcriptional and translational regulation in plant cells of the sequences encoding glycogen biosynthetic enzymes are of special interest. These constructs include, in the 5' to 3' direction of transcription, a transcriptional/translational initiation control region, a sequence encoding a glycogen biosynthetic enzyme in reading frame, and a transcription/translation termination region, wherein the sequence encoding the enzyme is under the regulatory control of the initiation and termination regions. Expression constructs may also contain sequences which encode a transit peptide that provides for translocation of the glycogen biosynthesis enzymes to plastids and/or a marker enzyme.

In another aspect of the invention, vectors are considered which comprise sequences providing for transfer of desired sequences and integration into the genome of a plant cell. For example a plant transformation vectors may include Agrobacterium T-DNA border region(s) to provide for transfer of the sequences to the plant cell.

Also considered part of this invention are plant cells containing nucleic acid sequences of a glycogen biosynthetic enzyme. Such plant cells are obtainable through plant transformation techniques which utilize Agrobacterium to transfer DNA to the plant cells or alternatively through direct transfer techniques such as electroporation, microinjection or DNA bombardment. In either case, plant cells containing the desired sequences can be regenerated to yield whole plants containing the sequences.

In yet another aspect of this invention, plant cells containing the glycogen biosynthetic enzymes or having reduced or increased starch precursor enzymes are considered. Of particular interest are plant cells in starch storage organs, such as roots, tubers or seeds. It is preferable that the enzyme be located in plastids, where starch synthesis occurs, and more preferably in amyloplasts, where reserve starch is synthesized and stored.

Further, it can be recognized that the modulation of glycogen biosynthetic enzymes in these plant cells has implications for modifying the starch content and/or composition of these cells. In this manner, plants or plant parts which synthesize and store starch may be obtained which have increased or decreased starch content and modified starch related properties such as specific gravity, free sugar content and/or novel and useful starches. In particular, potato starch having decreased amylose and modified amylopectin may be produced and further applications to modify starches consisting entirely of amylopectin such as that of waxy maize or a mutant potato, are also considered. Similarly, the starch from these plant parts can be harvested for use in commercial applications.

DETAILED DESCRIPTION OF THE INVENTION

This invention relates to glycogen biosynthesis enzymes in plants. In particular, this invention is directed to plant cells having a DNA sequence encoding a glycogen biosynthesis enzyme integrated in its genome as the result of genetic engineering. Cells containing a DNA or RNA (mRNA) sequence encoding the enzyme as well as cells containing the enzyme are also provided. Plants and, more particularly, plant parts may also be obtained which contain glycogen biosynthesis enzyme sequences and/or containing such glycogen biosynthesis enzymes.

The biosynthetic steps involved in glycogen synthesis in E. coli include: 1) the formation of ADP-glucose from ATP and glucose 1-phosphate, 2) the transfer of a glucose unit from ADP-glucose to a preformed maltodextrin primer via an $\alpha$1,4 linkage, and 3) the formation of $\alpha$1,6 glucosyl linkages from glycogen. The bacterial enzymes which catalyze the above reactions are ADP-glucose pyrophosphorylase (EC 2.7.7.27), glycogen synthase (EC 2.4.1.21), and Q-enzyme or branching enzyme (EC 2.4.1.18), respectively. The genes encoding these enzymes have been cloned and are also known as glgC, glgA, and glgB, respectively.

The pathway of glycogen biosynthesis in mammals is similar to that seen in bacteria, an exception being that UDP-glucose is the preferred glucose donor. The mammalian enzymes which catalyze glycogen biosynthetic reactions similar to those in bacteria are glucose-1-phosphate uridylyltransferase, glycogen synthase (EC 2.4.1.11), and 1,4-$\alpha$-glucan branching enzyme. Genes encoding a human muscle and a rat liver glycogen synthase have been cloned and their nucleic acid sequences determined.

In particular, the glycogen biosynthesis enzyme glycogen synthase (glgA) is of special interest. The E. coli glycogen synthase is of particular interest in that the enzyme is similar to plant starch synthase with respect to being non-responsive to allosteric effectors or chemical modifications. Expression of a glycogen synthase enzyme in a plant host demonstrates biological activity even within an intact plant cell. Namely, potato plants having glgA expressed in potato tubers result in tubers having a deceased specific gravity; specific gravity being a commonly used measurement with respect to dry matter and starch contents of potato tubers (W. G. Burton, in *The Potato*, Third Edition, pub. Longman Scientific and Technical (1989) Appendix II, pp. 599–601). Further analysis of transgenic tubers having decreased specific gravity indicates that the starch in these tubers is modified. In particular, the percentage of amylose is decreased and the ratio of low m.w./high m.w. chains in the amylopectin fraction is increased. This phenotypic effect in planta is indicative of glgA biological activity.

Other phenotypic starch modifications resulting from biological activity of glycogen biosynthetic enzymes in plants are also considered in this invention. Such altered phenotypes may result from enzymatic activity of these proteins on plant starch precursors, or alternatively from the inhibition of plant starch biosynthetic enzyme activities. Inhibition of plant enzymes, for example, could result through the production of inactive forms of the plant enzymes as the result of association with the glycogen biosynthetic enzymes. The inhibition of plant enzymes may then lead to plants having altered starch (such as branching patterns or molecular weight) and-/or lowered starch levels. In addition, increased plant metabolites, such as sugars, could also result from starch alteration or inhibition caused by expression of glycogen biosynthetic enzymes. For example, transgenic potato tubers described herein are observed to have up to 3-fold increases in free sugar content.

Measurement of specific gravity or free sugar content may be useful to detect modified starch, with other methods, such as HPLC and gel filtration, also being useful. The glycogen synthase sequence may be employed as the sole glycogen biosynthetic enzyme or in conjunction with sequences encoding other glycogen biosynthetic enzymes.

An enzyme relevant to the biosynthesis of glycogen is considered in this invention as including any sequence of amino acids, such as protein, polypeptide, or peptide fragment, which demonstrates the ability to catalyze a reaction involved in the biosynthesis of glycogen. Thus, a glycogen biosynthetic enzyme of this invention will display activity towards a glucan molecule, although it may have preferential activity towards either ADP- or UDP-glucose. In plants, ADP-glucose is the preferred donor for starch biosynthetic reactions. Therefore, of particular interest in this invention are glycogen biosynthesis enzymes which also prefer ADP-glucose. Of special interest are glycogen biosynthesis enzymes obtainable from bacterial sources. Over 40 species of bacteria synthesize glycogen, including Escherichia and Salmonella.

Obtaining glycogen biosynthetic enzymes may be accomplished by a variety of methods known to those skilled in the art. For example, radiolabeled nucleic acid probes may be prepared from a known sequence which will bind to and thus provide for detection of other sequences, glycogen biosynthesis proteins may be purified and sequences obtained through biochemical or antibody techniques, polymerase chain reaction (PCR) may be employed based upon known nucleic acid sequences, and the like.

Typically, a sequence obtainable from the use of nucleic acid probes will show 60–70% sequence identity between the target sequence and the given sequence encoding a glycogen biosynthetic enzyme of interest. However, lengthy sequences with as little as 50–60% sequence identity may also be obtained. The nucleic acid probes may be a lengthy fragment of the nucleic acid sequence, or may also be a shorter, oligonucleotide probe. Oligonucleotide probes can be considerably shorter than the entire nucleic acid sequence encoding a glycogen biosynthetic enzyme, but should be at least about 10, preferably at least about 15, and more preferably at least about 20 nucleotides. A higher degree of sequence identity is desired when shorter regions are used as opposed to longer regions. It may thus be desirable to identify enzyme active sites where amino acid sequence identity is high to design oligonucleotide probes for detecting homologous genes.

When longer nucleic acid fragments are employed as probes (greater than about 100 bp), one may screen at lower stringencies in order to obtain sequences from the target sample which have 20–50% deviation (i.e., 50–80 sequence homology) from the sequences used as probe. Hybridization and washing conditions can be varied to optimize the hybridization of the probe to the sequences of interest. Lower temperatures and higher salt (SSC) concentrations allow for hybridization of more distantly related sequences (low stringency). If background hybridization is a problem under low stringency conditions, the temperature can be raised either in the hybridization or washing steps and/or salt content lowered to improve detection of the specific hybridizing sequence. Hybridization and washing temperatures can be adjusted based on the estimated melting temperature of the probe. (See, for example, Beltz, et al. *Methods in Enzymology* (1983) 100:266–285).

It will be recognized by one of ordinary skill in the art that glycogen biosynthetic enzyme sequences of this invention may be modified using standard techniques of site specific mutation or PCR, or modification of the sequence may be accomplished in producing a synthetic nucleic acid sequence and will still be considered a glycogen biosynthesis enzyme nucleic acid sequence of this invention. For example, wobble positions in codons may be changed such that the nucleic acid sequence encodes the same amino acid sequence, or alternatively, codons can be altered such that conservative amino acid substitutions result. In either case, the peptide or protein maintains the desired enzymatic activity and is thus considered part of the instant invention.

A nucleic acid sequence of an enzyme relevant to the biosynthesis of glycogen of this invention may be a DNA or RNA sequence, derived from genomic DNA, cDNA, mRNA, or may be synthesized in whole or in part. The structural gene sequences may be cloned, for example, by isolating genomic DNA from an appropriate source, and amplifying and cloning the sequence of interest using a polymerase chain reaction (PCR). Alternatively, the gene sequences may be synthesized, either completely or in part, especially where it is desirable to provide plant-preferred sequences. Thus, all or a portion of the desired structural gene may be synthesized using codons preferred by a selected plant host. Plant-preferred codons may be determined, for example, from the codons used most frequently in the proteins expressed in a particular plant host species. Other modifications of the gene sequences may result in mutants having slightly altered activity. Once obtained, a glycogen biosynthetic enzyme nucleic acid sequence of this invention may be combined with other sequences in a variety of ways.

Often, the sequences associated with glycogen biosynthesis are used in conjunction with endogenous plant sequences. By "endogenous plant sequence" is meant any sequence which can be naturally found in a plant cell. These sequences include native (indigenous) plant sequences as well as sequences from plant viruses or plant pathogenic bacteria, such as Agrobacterium or Rhizobium species that are naturally found and functional in plant cells.

In one aspect of this invention, the glycogen biosynthesis enzyme will be joined to a sequence encoding a transit peptide or functional portion of a transit peptide which is capable of providing for intracellular transport of a heterologous protein to a plastid in a plant host cell. Chloroplasts are the primary plastid in photosynthetic tissues, although plant cells are likely to have other kinds of plastids, including amyloplasts, chromoplasts, and leucoplasts. Transport into amyloplasts is preferred in this invention as these plastids are associated with reserve starch synthesis and storage. Any transit peptide providing for intracellular transport to a plastid is useful in this invention, such as the transit peptides from the precursor proteins of the small subunit of ribulose bisphosphate carboxylase (RUBISCO), acyl carrier protein (ACP), the waxy locus of maize, or other nuclear-encoded plastid proteins.

In addition to the identified transit peptide portion of a protein, it may be desirable to include sequences encoding a portion of the mature plastid-targeted protein to facilitate the desired intracellular transport of the glycogen biosynthetic enzyme. In one embodiment of this invention, the transit peptide from the small subunit of RUBISCO is utilized along with 48 bp of sequence encoding the amino terminal 16 amino acids of a mature small subunit protein.

Other endogenous plant sequences may be provided in nucleic acid constructs of this invention, for example to provide for transcription of the glycogen biosynthetic enzyme sequences. Transcriptional regulatory regions are located immediately 5' to the DNA sequences of the gene of interest, and may be obtained from sequences available in the literature, or identified and characterized by isolating genes having a desirable transcription pattern in plants, and studying the 5' nucleic acid sequences. Numerous transcription initiation regions which provide for a variety of constitutive or regulatable, e.g. inducible, expression in a plant cell are known. Among sequences known to be useful in providing for constitutive gene expression are regulatory regions associated with Agrobacterium genes, such as for nopaline synthase (Nos), mannopine synthase (Mas), or octopine synthase (Ocs), as well as regions coding for expression of viral genes, such as the 35S and 19S regions of cauliflower mosaic virus (CaMV). The term constitutive as used herein does not necessarily indicate that a gene is expressed at the same level in all cell types, but that the gene is expressed in a wide range of cell types, although some variation in abundance is often detectable. Other useful transcriptional initiation regions preferentially provide for transcription in certain tissues or under certain growth conditions, such as those from napin, seed or leaf ACP, the small subunit of RUBISCO, patatin, zein, and the like.

Sequences to be transcribed are located 3' to the plant transcription initiation region and may be oriented, in the 5'-3' direction, in the sense orientation or the antisense orientation. In the sense orientation, an mRNA strand is produced which encodes the desired glycogen biosynthetic enzyme, while in antisense constructs, an RNA sequence complementary to an enzyme coding sequence is produced. The sense orientation is desirable when one wishes to produce the glycogen biosynthetic enzyme in plant cells, whereas the antisense strand may be useful to inhibit production of a related plant starch biosynthesis enzymes. Regions of homology have been observed, for example, upon comparison of E. coli glgC sequence to that of a rice ADP glucose pyrophosphorylase. Either method may be useful in obtaining an alteration in the starch or dry matter content of a plant. The presence of glycogen biosynthetic enzyme sequences in the genome of the plant host cell may be confirmed, for example by a Southern analysis of DNA or a Northern analysis of RNA sequences or by PCR methods.

In addition to sequences providing for transcriptional initiation in a plant cell, also of interest are sequences which provide for transcriptional and translational initiation of a desired sequence encoding a glycogen biosynthetic enzyme. Translational initiation regions may be provided from the source of the transcriptional initiation region or from the gene of interest. In this manner, expression of the glycogen biosynthetic enzyme in a plant cell is provided. The presence of the glycogen biosynthetic enzyme in the plant host cell may be confirmed by a variety of methods including a immunological analysis of the protein (e.g. Western or ELISA), as a result of phenotypic changes observed in the cell, such as altered starch content, altered starch branching, etc., or by assay for increased enzyme activity, and the like.

If desired the enzyme may be harvested from the plant host cell or used to study the effect of the enzyme on plant cell functions, especially in the plastid organelles.

Other sequences may be included in the nucleic acid construct providing for expression of the glycogen biosynthetic enzymes ("expression constructs") of this invention, including endogenous plant transcription termination regions which will be located 3' to the desired glycogen biosynthetic enzyme encoding sequence. In one embodiment of this invention, transcription termination sequences derived from a patatin gene are preferred. Transcription termination regions may also be derived from genes other than those used to regulate the transcription in the nucleic acid constructs of this invention. Transcription termination regions may be derived from a variety of different gene sequences, including the Agrobacterium, viral and plant genes discussed above for their desirable 5' regulatory sequences.

Further constructs are considered which provide for transcription and/or expression of more than one glycogen biosynthetic enzyme. For example, one may wish to provide enzymes to plant cells which provide for modification of the starch synthesized, as well as for an increase or decrease in overall starch production. Examples of enzymes which may prove useful in modifying starch structure are those which catalyze reactions involving UDP- or ADP-glucose, for example glycogen synthase or branching enzyme. However, to provide for increased or decreased starch production, one may wish to utilize sequences encoding enzymes which catalyze formation of the nucleotide-glucose molecule, such as ADP-glucose pyrophosphorylase in bacteria, or glucose-1-phosphate uridylyltransferase in mammals. Although plants typically utilize ADP-glucose, UDP-glucose may also be useful.

In providing for transcription and/or expression of the glycogen biosynthetic enzyme sequences, one may wish to limit these enzymes to plant cells which synthesize and store reserve starch. Towards this end, one can identify useful transcriptional initiation regions that provide for expression preferentially in the roots, tubers, seeds, or other starch-containing tissues of a desired plant species. These sequences may be identified from cDNA libraries using differential screening techniques, for example, or may be derived from sequences known in the literature. Of particular interest in a presently preferred embodiment of the invention is a transcriptional initiation region from the patatin gene of potato, which demonstrates preferential expression in the potato tuber. Similarly, other promoters which are preferentially expressed in the starch-containing tissues, such as the zein genes in corn, as opposed to other plant structures are desirable.

In developing the nucleic acid constructs of this invention, the various components of the construct or fragments thereof will normally be inserted into a convenient cloning vector, e.g. a plasmid, which is capable of replication in a bacterial host, e.g. E. coli. Numerous vectors exist that have been described in the literature, many of which are commercially available. After each cloning, the cloning vector with the desired insert may be isolated and subjected to further manipulation, such as restriction, insertion of new fragments or nucleotides, ligation, deletion, mutation, resection, etc. so as to tailor the components of the desired sequence. Once the construct has been completed, it may then be transferred to an appropriate vector for further manipulation in accordance with the manner of transformation of the host cell.

The constructs of this invention providing for transcription and/or expression of glycogen biosynthetic enzyme sequences of this invention may be utilized as vectors for plant cell transformation. The manner in which nucleic acid sequences are introduced into the plant host cell is not critical to this invention. Direct DNA transfer techniques, such as electroporation, microinjection or DNA bombardment may be useful. To aid in identification of transformed plant cells, the constructs of this invention may be further manipulated to include plant selectable markers. The use of plant selectable markers is preferred in this invention as the amount of experimentation required to detect plant cells is greatly reduced when a selectable marker is expressed. Useful selectable markers include enzymes which provide for resistance to an antibiotic such as gentamycin, hygromycin, kanamycin, and the like. Similarly, enzymes providing for production of a compound identifiable by color change, such as GUS, or luminescence, such as luciferase are useful.

An alternative method of plant cell transformation employs plant vectors which contain additional sequences which provide for transfer of the desired glycogen biosynthetic enzyme sequences to a plant host cell and stable integration of these sequences into the genome of the desired plant host. Selectable markers may also be useful in these nucleic acid constructs to provide for differentiation of plant cells containing the desired sequences from those which have only the native genetic material. Sequences useful in providing for transfer of nucleic acid sequences to host plant cells may be derived from plant pathogenic bacteria, such as Agrobacterium or Rhizogenes, plant pathogenic viruses, or plant transposable elements.

When Agrobacterium is utilized for plant transformation, it may be desirable to have the desired nucleic acid sequences bordered on one or both ends by T-DNA, in particular the left and right border regions, and more particularly, at least the right border region. These border regions may also be useful when other methods of transformation are employed.

Where Agrobacterium or Rhizogenes sequences are utilized for plant transformation, a vector may be used which may be introduced into an Agrobacterium host for homologous recombination with the T-DNA on the Ti- or Ri-plasmid present in the host. The Ti- or Ri-containing the T-DNA for recombination may be armed (capable of causing gall formation), or disarmed (incapable of causing gall formation), the latter being permissible so long as a functional complement of the vir genes, which encode trans-acting factors necessary for transfer of DNA to plant host cells, is present in the transformed Agrobacterium host. Using an armed Agrobacterium strain can result in a mixture of normal plant cells, some of which contain the desired nucleic acid sequences, and plant cells capable of gall formation due to the presence of tumor formation genes. Cells containing the desired nucleic acid sequences, but lacking tumor genes can be selected from the mixture such that normal transgenic plants may be obtained.

In a preferred method where Agrobacterium is used as the vehicle for transforming host plant cells, the expression or transcription construct bordered by the T-DNA border region(s) will be inserted into a broad host range vector capable of replication in *E. coli* and Agrobacterium, there being broad host range vectors described in the literature. Commonly used is pRK2 or derivatives thereof. See, for example, Ditta, et al., (*Proc. Nat. Acad. Sci., U.S.A.* (1980) 77:7347–7351) and EPA 0 120 515, which are incorporated herein by reference. Alternatively, one may insert the sequences to be expressed in plant cells into a vector containing separate replication sequences, one of which stabilizes the vector in *E. coli*, and the other in Agrobacterium. See, for example, McBride and Summerfelt (*Plant Mol. Biol.* (1990) 14:269–276), wherein the pRiHRI (Jouanin, et al., *Mol. Gen. Genet.* (1985) 201:370–374) origin of replication is utilized and provides for added stability of the plant expression vectors in host Agrobacterium cells.

Utilizing vectors such as those described above, which can replicate in Agrobacterium is preferred. In this manner, recombination of plasmids is not required and the host Agrobacterium vir regions can supply trans-acting factors required for transfer of the T-DNA bordered sequences to plant host cells.

In general, the plant vectors of this invention will contain glycogen biosynthetic enzyme sequence(s), alone or in combination with transit peptides, and endogenous plant sequences providing for transcription or expression of these sequences in a plant host cell. The plant vectors containing the desired sequences may be employed with a wide variety of plant cells, particularly plants which produce and store reserve starch. Plants of interest include, but are not limited to corn, cereal grains, sorghum, rice, potato, tapioca, cassava, arrowroot and sago.

Also considered part of this invention are plants containing the nucleic acid sequences of this invention, and following from that, plants containing glycogen biosynthetic enzymes as the result of expression of the sequences of this invention in plant cells or having a decreased expression of a native starch biosynthesis enzyme. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations either from seed or using vegetative propagation techniques.

Of particular interest are plant parts, e.g. tissues or organs, (and corresponding cells) which form and store reserve starch, such as roots, tubers, and seeds. Of more particular interest are potato tubers containing the glycogen biosynthetic enzymes. It can be recognized that the modification of glycogen biosynthetic enzymes in plants may also result in desirable alterations in the plant cells or parts. These alterations may include modification of dry matter content, free sugar content or of starch content and/or structure, or modification of specific gravity. The novel plant cells or plant parts can thus be harvested and used for isolation of the altered material.

The invention now being generally described, it will be more readily understood by reference to the following examples which are included for purposes of illustration only and are not intended to limit the present invention.

EXAMPLES

EXAMPLE 1

Cloning of Glycogen Biosynthetic Enzyme Genes

A. Cloning and Sequencing of a GlgA Gene From *E. coli*

Total genomic DNA is prepared from *E. coli* K12 618 (Leung et al., *J. of Bacteriology* (1986) 167:82–88) by growing a 5 ml culture in ECLB (Maniatis, T. et al., *Molecular Cloning: A Laboratory Manual*, (1982) Cold Spring Harbor, N.Y.) overnight at 37° C. The bacteria are pelleted by centrifugation for 10 minutes at 4500×g, the supernatant is discarded, and the pellet is resuspended in 2.5 ml of 10 mM Tris, 1 mM EDTA buffer. To this suspension is added 500 µl of a 5 mg/ml Pronase ® protease (Calbiochem Brand Biochemicals; La Jolla, Calif.) solution and 2 ml of 2% lauryl sulfate, sodium salt (Sigma; St. Louis, Mo.), with gentle mixing, and the suspension is incubated at 37° C. for 50 minutes. A clear solution indicates that the bacteria have lysed. The solution is then extracted with 5 ml phenol, then 5 ml phenol: chloroform: isoamyl alcohol (25:24:1) , followed by 5 ml chloroform. Nucleic acids are precipitated from the aqueous phase with 1/10 volume of 3M sodium acetate and two volumes of 100% ethanol, and the tube is incubated at room temperature for 1 hour. Nucleic acids are removed from solution and resuspended in 1 ml water. A second ethanol precipitation is performed and the nucleic acids are resuspended in 200 µl of 10 mM Tris, 1 mM EDTA buffer.

Synthetic oligonucleotides, str1 and str2, corresponding to sequences flanking the 1.4 kb glgA (glycogen synthase—EC 2.4.1.21) gene of *E. coli* (Kumar et al., *J. of Biol. Chemistry* (1986) 261:16256–16259) and containing restriction sites for BglII (str1) and SalI (str2) are synthesized on an Applied Biosystems 380A DNA synthesizer (Foster City, Calif.) in accordance with the manufacturer's instructions.

The nucleic acid preparation of *E. coli* is treated with RNAse and the DNA is used as a template in a polymerase chain reaction (PCR) with str1 and str2 as primers. A Perkin-Elmer/Cetus (Norwalk, Conn.) thermal cycler is used with the manufacturer's reagents and in accordance with the manufacturer's instructions. The reaction mixture contains 41.5 µl H2O, 10 µl 10X reaction buffer, 16 µl dNTP's [1.25 mM dCTP, dATP, dGTP and dTTP], 5 µl str1 (20 mM), 5 µl str2 (20 mM), 22 µl total *E. coli* DNA (0.05 µg/µl), and 0.5 µl Taq polymerase. The reaction is performed for 15 cycles with melting (denaturation) for 1 minute at 94° C. annealing (hybridization) for 2 minutes at 37° C. and chain elongation for 3 minutes at 72° C. The reaction is then performed for an additional 10 cycles with melting for 1 minute at 94° C., annealing for 2 minutes at 37° C. and chain elongation at 72° C. for 3 minutes 15 seconds initially and increasing the time by 15 seconds each cycle so that the last cycle is 5 minutes 45 seconds.

The resulting PCR products (~1.4 kb) are digested with BglII and SalI and ligated into a SalI and BglII digest of pCGN789, a pUC based vector similar to pUC119 with the normal polylinker replaced by a synthetic linker which contains the restriction digest sites EcoRI, SalI, BglII, PstI, XhoI, BamHI, and HindIII. The ligated DNA is transformed into *E. coli* DH5α. The transformed cells are plated on ECLB containing penicillin (300 mg/L), IPTG and X-Gal (Vieira and Messing Gene (1982) 19:259–268). White colonies are picked to ECLB containing penicillin (300 mg/L) and flooded with I2/KI (0.2% I2 in 0.4% KI). Clones producing a brown color, which indicates excess starch production, are selected. One clone, glgA-2, was selected and the DNA and translated amino acid sequences determined (see, FIGS. 1 and 2 and SEQ ID NOS: 1-2). The DNA sequence is 98% homologous to the published sequence (Kumar et al, supra) and 96% homologous at the amino acid level.

B. Cloning and Sequencing of a GlgC Gene From *E. coli*

Synthetic oligonucleotides, glgC1 and glgC2, corresponding to sequences flanking the 1.3 kb glgC (ADP-glucose pyrophosphorylase—EC 2.7.7.27) gene of *E. coli* (Baecker et al., *J. of Biol. Chemistry* (1983) 258:5084–5088) and containing restriction sites for BglII (glgC1) and SalI (glgC2) are synthesized on an Applied Biosystems 380A DNA synthesizer (Foster City, Calif.) in accordance with the manufacturer's instructions.

Total genomic DNA is prepared from *E. coli* K12 618 as described above. The nucleic acid preparation of *E. coli* is treated with RNAse and the DNA is used as a template in a polymerase chain reaction (PCR) with glgC1 and glgC2 as primers. A Perkin-Elmer/Cetus (Norwalk, Conn.) thermal cycler is used with the manufacturer's reagents as described above.

The resulting PCR products (~1.3 kb) are digested with BglII and SalI and ligated into a SalI and BglII digest of pCGN789 (described above). The ligated DNA is transformed into *E. coli* DH5α, and the transformed cells are plated as described above. Clones producing excess starch are selected as described above. One clone, pGlgC-37, was selected and the DNA sequence (SEQ ID NO: 3) determined (see, FIG. 3). The DNA sequence is 99% homologous to the published sequence (Baecker et al, supra) of glgC from *E. coli* K-12. The glgC from *E. coli* 618 is a mutant and the amino acid sequence of this mutant differs from that of *E. coli* K-12 at five amino acids (Lee et al., *Nucl. Acids Res.* (1987) 15:10603). The translated amino acid sequence of pGlgC-37 differs from that of the glgC from *E. coli* 618 at a single amino acid; the asparagine (Asn) at position 361 of the *E. coli* 618 mutant is an aspartate (Asp) in the translated amino acid sequence of pGlgC-37 (FIG. 3).

EXAMPLE 2

Attachment of Glycogen Genes to SSU Leader Sequence

A. Construction of SSU+aroA Transit Peptide

Plasmid pCGN1132 contains a 35S promoter, ribulosebisphosphate carboxylase small subunit (5'-35S-SSU) leader from soybean plus 48 bp of mature small subunit (SSU) gene from pea, and aroA sequence (the gene locus which encodes 5-enolpyruvyl-3-phosphoshikimate synthetase (EC 2.5.1.19)). It is prepared from pCGN1096, a plasmid containing a hybrid SSU gene, which carries DNA encoding mature SSU protein from pea, and SstI and EcoRI sites 3' of the coding region (used in the preparation of pCGN1115, a plasmid having a 5'-35S-SSU+48-aroA-tml-3' sequence) and pCGN1129, (a plasmid having a 35S promoter in a chloramphenicol resistance gene (Cam$^r$) backbone).

Construction of pCGN1096

The aroA moiety of pCGN1077 is removed by digestion with SphI and SalI. (The construction of pCGN1077 and other constructs hereunder are described in detail in co-pending U.S. application Ser. No. 07/097,498, filed Sep. 16, 1987, now abandoned, which is hereby incorporated by reference). In its place is cloned the region coding for the mature pea SSU protein, as an SphI-PstI fragment, which is then excised with SphI and SalI. The resulting plasmid, pCGN1094, codes for a hybrid SSU protein having the transit peptide of the soybean clone, and the mature portion of the pea clone and contains SstI and EcoRI sites 3' of the coding region. The HindIII to BamHI region of transposon Tn6 (Jorgensen et al., *Mol. Gen. Genet.* (1979) 177:65) encoding the kanamycin resistance gene (Kan$^r$) is cloned into the same sites of pBR322 (Bolivar et al., *Gene* (1977) 2:95–133) generating pDS7. The BglII site 3' of the Kan$^r$ gene is digested and filled in with the large fragment of *E. coli* DNA polymerase 1 and deoxynucleotides triphosphate. An SstI linker is ligated into the blunted site, generating plasmid pCGN1093. Plasmid pPMG34.3 is digested with SalI, the site filled in as above and EcoRI linkers are ligated into the site resulting in plasmid pCGN1092. The latter plasmid is digested with SstI and SmaI and the Kan$^r$ gene excised from pCGN1093 with SstI and SmaI is ligated in, generating pCGN1095. The Kan$^r$ and aroA genes are excised as a piece from pCGN1095 by digestion with SstI and EcoRI and inserted into the SstI and EcoRI sites of pCGN1094, producing pCGN1096. Summarizing, pCGN1096 contains (5'–3') the following pertinent features: The SSU gene—a polylinker coding for PstI, SalI, SstI, and KpnI—the Kan$^r$ gene—SmaI and BamHI restriction sites—the aroA gene without the original ATG start codon.

Construction of pCGN1115

Plasmid pCGN1096 is digested to completion with SalI and then digested with exonuclease Bal31 (BRL; Gaithersburg, Md.) for 10 minutes, thus deleting a portion of the mature SSU gene. The resulting plasmid is then digested with SmaI to eliminate the Kan$^r$ gene and provide blunt ends, recircularized with T4 DNA ligase and transformed into *E. coli* LC3 (Comai et al., *Science* (1983) 221:370–371), an aroA mutant. DNA isolated from aroA+ and Kan$^r$ colonies is digested with BamHI and SphI and ligated with BamHI- and SphI-digested M13mp18 (Norrander et al., *Gene* (1983) 26:101–106 and Yanisch-Perron et al., *Gene* (1985) 33: 103–119) DNA for sequencing. Clone 7 has 48 bp of the mature SSU gene remaining and the 3' end consists of phe-glu-thr-leu-ser (SEQ ID NO: 4). Clone 7 is transformed into *E. coli* strain 71-18 (Yanish-Perron et al. (1985) supra) and DNA isolated from transformants is digested with SphI and ClaI to remove the 0.65 kb fragment containing the 48 bp of mature protein and the 5' end of the aroA gene. Plasmid pCGN1106 (Comai, L. et al., *J. Biol. Chem.* (1988) 263:15104–15109) is also digested with SphI and ClaI and the 6.8 kb isolated vector fragment is ligated with the 0.65 kb fragment of clone 7 to yield pCGN1115 (5'-35S-SSU+48-aroA-tml-3').

Construction of pCGN1129

The 7.2 kb plasmid pCGN1180 (35S-SSU+70-aroA-ocs3') (Comai et al. (1988) supra) and the 25.6 kp plasmid pCGN594 (LB-Gent$^r$-ocs5'-Kan$^r$-ocs3'-RB) (construction of pCGN594 is described in co-pending U.S. application Ser. No. 07/382,802, filed Jul. 19, 1989, now abandoned) are digested with HindIII and ligated together to yield the 32.8 kb plasmid pCGN1109 (LB-Gent$^r$-35S-SSU+70-aroA-ocs3'-ocs5'-Kan$^r$-ocs3'-RB).

Plasmid pCGN1109 is digested with EcoRI to delete an internal 9.1 kb fragment containing the SSU leader plus 70 bp of the mature SSU gene, the aroA gene and its ocs3' terminator, the Amp$^r$ backbone from pCGN1180 and ocs5'-Kan$^r$-ocs3' from pCGN594. The EcoRI digest of pCGN1109 is then treated with Klenow fragment to blunt the ends, and an XhoI linker (dCCTCGAGG) (New England Biolabs.; Beverly, Mass.) is ligated in, yielding pCGN1125 (LB-35S-RB).

Plasmid pCGN1125 is digested with HindIII and BglII to delete the 0.72 kb fragment of the 35S promoter. This digest is ligated with HindIII- and BamHI-digested Cam$^r$ vector, pCGN786 (described in co-pending U.S. application Ser. No. 07/382,803, filed Jul. 19, 1989). The resulting 3.22 kb plasmid, pCGN1128, contains the 35S promoter with a 3' multilinker in a Cam$^r$ backbone.

Plasmid pCGN1128 is digested with HindIII, treated with Klenow fragment to blunt the ends and ligated with BglII linkers to yield pCGN1129, thus changing the HindIII site located 5' to the 35S promoter into a BglII site.

B. Transit Peptide Joined to GlgA Gene

Plasmid pCGN1115 is digested with SalI to remove a 1.6 kb fragment containing the SSU leader plus 48 bp of the mature SSU gene and the aroA gene. An XhoI digest of pCGN1129 opens the plasmid 3' to the 35S promoter. Ligation of these two digests yields the 4.8 kb plasmid pCGN1132, containing 5'-35S-SSU leader plus 48 bp of mature SSU-aroA.

Plasmid pGlgA-2 is digested with BglII and SalI and ligated to pCGN1132 that has been digested with BamHI and SalI. A clone containing 5' 35S-SSU+48bp-glgA 3' is selected and designated pCGN1439.

C. Transit Peptide Joined to GlgC Gene

Plasmid pGlgC-37 is digested with BglII and SalI and ligated to pCGN1132 that has been digested with BamHI and SalI. A clone containing 5'35S-SSU+48bp-glgC 3' is selected and designated pCGN1440.

EXAMPLE 3

Cloning of Patatin Regulatory Regions and Preparation of Patatin-5'-nos-3' Expression Cassettes This example describes the cloning of a patatin-5' regulatory region from potato and the preparation of patatin-5'-nos-3' expression cassette pCGN2143.

Genomic DNA is isolated from leaves of *Solanum tuberosum* var. Kennebec as described in Dellaporta et al., *Plant Mol. Biol. Reporter* (1983) 1(4):19–21), with the following modifications: approximately 9 g fresh weight of leaf tissue is ground, a polytron grinding is not performed and in the final step the DNA is dissolved in 300 μl of 10 mM Tris, 1 mM EDTA, pH 8.

A synthetic oligonucleotide, pat1, containing digestion sites for NheI, PstI and XhoI with 24 bp of homology to the 5'-region of a 701 bp fragment (coordinates 1611 to 2313) 5' to a class I patatin gene, isolated from *Solanum tuberosum* var. Maris Piper (Bevan et al., *NAR* (1986) 14:4625–4638), is synthesized (Applied BioSystems 380A DNA synthesizer). A second synthetic oligonucleotide, pat2, containing digestion sites for BamHI and SpeI with 25 bp of homology to the 3' region of the 703 bp piece is also synthesized.

Using the genomic potato DNA as a template, and pat1 and pat2 as primers, a polymerase chain reaction (PCR) is performed in a Perkin-Elmer/Cetus thermal cycler with the manufacturer's reagents and in accordance with the manufacturer's instructions. The reaction contains 62.5 μl H₂O, 10 μl 10X Reaction buffer, 16 μl dNTP's [1.25 mM dCTP, dATP, dGTP and dTTP], 5 μl pat1 (20 mM), 5 μl pat2 (20 mM), 1 μl potato genomic DNA (3 μg/μl), 0.5 μl Tag polymerase. The PCR is performed for 25 cycles with melting for 1 minute at 94° C., annealing for 2 minutes at 37° C. and chain elongation for 3 minutes at 72° C. The resulting PCR product fragments (approximately 700 bp) are digested with NheI and BamHI. Plasmid pCGN1586N ('5-D35S-TMVΩ'-nos-3'; pCGN1586 (described below) having a NheI site 5' to the 35S region) is digested with NheI and BamHI to delete the D35S-Ω' fragment. Ligation of NheI-BamHI digested pCGN1586N, which contains the nos-3' region, and the PCR fragments yields a patatin-5'-nos3' cassette with SpeI, BamHI, SalI and SstI restriction sites between the 5' and 3' regions for insertion of a DNA sequence of interest.

The 5' region of a clone, designated pCGN2143 is sequenced. Plasmid pCGN2143 has a Kennebec patatin-5' region that is 702 bp in length and 99.7% homologous to the native sequence (as reported by Bevan (1986) supra).

Synthetic oligonucleotides, pat5 and pat6, are prepared as described above. Pat5 and pat6 contain complementary sequences which contain the restriction digest sites NheI, XhoI and PstI. Pat5 and pat6 are annealed to create a synthetic linker. The annealed linker is ligated to pCGN2143 that has been linearized with EcoRI and treated with Klenow polymerase to generate blunt ends. A plasmid, pCGN2162 which has the following restriction sites at the 3' end of nos is selected:

5'-EcoRI-NheI-XhoI-PstI-EcoRI.

Construction of pCGN1586/1586N

Plasmid pCGN2113 (6.1 kb) contains a double-35S promoter (D35S) and the tml-3' region with multiple cloning sites between them, contained in a pUC-derived plasmid backbone bearing an ampicillin resistance gene (Ampr). The promoter/tml cassette is bordered by multiple restriction sites for easy removal. Plasmid pCGN2113 is digested with EcoRI and SacI, deleting the 2.2 kb tml-3' region. Plasmid pBI221.1 (Jefferson, R. A., *Plant Mol. Biol. Reporter* (1987) 5:387–405) is digested with EcoRI and SacI to delete the 0.3 kb nos-3' region. The digested pCGN2113 and pBI221.1 DNAs are ligated together, and the resultant 4.2 kb recombinant plasmid with the tml-3' of pCGN2113 replaced by nos-3' is designated pCGN1575 (5'-D35S-nos-3').

Plasmid pCGN1575 is digested with SphI and XbaI, blunt ends generated by treatment with Klenow fragment, and the ends are ligated together. In the resulting plasmid, pCGN1577, the SphI, PstI, SalI and XbaI sites 5' of the D35S promoter are eliminated.

Plasmid pCGN1577 is digested with EcoRI, the sticky ends blunted by treatment with Klenow fragment, and synthetic BglII linkers (d(pCAGATCTG) New England Biolabs, Inc.; Beverly, Mass.) are ligated in. A total of three BglII linkers are ligated into the EcoRI site creating two PstI sites. The resulting plasmid, termed pCGN1579 (D35S-nos-3'), has a 3' polylinker consisting of 5'-EcoRI, BglII, PstI, BglII,PstI, BglII, EcoRI-3'.

A tobacco mosaic virus omega' (TMVΩ') region (Gallie et al., *NAR* (1987) 15(21):8693–8711) with BglII, NcoI, BamHI, SalI and SacI restriction sites:

```
              BglII
5'-CAGGAGATCT TATTTTTACA ACAATTACCA ACAACAACAA ACAACAAACA
ACATTACAAT TACTATTTAC AATTACACCA TGGATCCGCTC GACGAGCTC 3'
(SEQ ID NO: 5)              NcoI  BamHI  SalI    SacI
``` is synthesized on an Applied Biosystems ® 380A DNA synthesizer and digested with BglII and SacI. Plasmid pCGN1577 is digested with BamHI and SacI and the synthetic TMVΩ' is ligated in between the 5'-D35S and nos-3' regions. The resulting plasmid is designated pCGN1586 (5'-D35S-TMVΩ'-nos-3'). Plasmid pCGN1586N is made by digesting pCGN1586 with HindIII and filling in the 5' overhang with Klenow fragment, thus forming a NheI site 5' to the D35S region.

pCGN2143 is also described in co-pending U.S. application Ser. No. 07/536,392 filed Jun. 11, 1990, now abandoned, which is hereby incorporated by reference.

EXAMPLE 4

Preparation of Binary Vectors

This example describes the construction of a binary vector containing: (1) the patatin-5' region from *Solanum tuberosum* var. Kennebec, (2) DNA encoding a transit peptide from soybean RuBisCo SSU protein, (3) 48 bp of DNA encoding 16 amino acids of mature RuBisCo SSU protein from pea, (4) the glgA coding region from *E. coli* 618 and (5) the nos-3' region.

A. GlgA Construct

Plasmid pCGN2162 prepared as described in Example 3 is digested with SpeI and SalI, opening the plasmid between the patatin-5' region and nos-3' region. Plasmid pCGN1439 (described in Example 2) is digested with XbaI and SalI and ligated with pCGN2162 to yield pCGN1454. Plasmid pCGN1454 consists of 5'-Kennebec patatin-SSU+48-glgA-nos3'.

pCGN1454 is digested with XhoI and treated with Klenow polymerase to generate blunt ends. pCGN1557 is digested with XbaI and treated with Klenow polymerase to generate blunt ends. The fragments resulting from the digests are ligated together. The transformation is plated onto ECLB containing gentamycin, IPTG and X-Gal. White colonies are picked and screened for ampicillin sensitivity Gent$^r$, Amp$^s$ clones are analyzed and two clones are selected. pCGN1457 has the 5'patatin-SSU+48bp-glgA-nos3' inserted into pCGN1557 such that it transcribes in the opposite direction from the 35S-Kan$^r$-tml gene. pCGN1457B has the 5'patatin-SSU+48bp-glgA-nos3' inserted into pCGN1557 such that it transcribes in the same direction as the 35S-Kan$^r$-tml gene.

B. GlgC Construct

Plasmid pCGN2162 prepared as described in Example 3 is digested with SpeI and SalI, opening the plasmid between the patatin-5' region and nos-3' region. Plasmid pCGN1440 (described in Example 2) is digested with XbaI and SalI and ligated with pCGN2162 to yield pCGN1453. Plasmid pCGN1453 consists of 5'-Kennebec patatin-SSU+48-glgC-nos3'.

pCGN1453 is digested with PstI and ligated to a PstI digest of pCGN1557. The transformation is plated as described above and colonies are screened for ampicillin sensitivity. Gent$^r$, Amp$^s$ clones are analyzed and one clone, pCGN1455, is selected. pCGN1455 has the 5'patatin-SSU+48bp-glgC-nos3' inserted into pCGN1557 such that it transcribes in the same direction as the 35S-Kan$^r$-tml gene.

C. Construction of pCGN1557

Plasmid pCGN1557 (McBride and Summerfelt, *Plant Mol. Biol.* (1990) 14(27):269–276) is a binary plant transformation vector containing the left and right T-DNA borders of *Agrobacterium tumefaciens* octopine Ti-plasmid pTiA6 (Currier and Nester, *J. Bact.* (1976) 126:157–165), the gentamicin resistance gene (Gen$^r$) of pPH1JI (Hirsch and Beringer, *Plasmid* (1984) 12:139–141), an *Agrobacterium rhizogenes* Ri plasmid origin of replication from pLJbB11 (Jouanin et al., *Mol. Gen. Genet.* (1985) 201:370–374), a 35S promoter-Kan$^r$-tml-3' region capable of conferring kanamycin resistance to transformed plants, a ColE1 origin of replication from pBR322 (Bolivar et al. (1977) supra) and a lacZ' screenable marker gene from pUC18 (Yanisch-Perron et al., (1985) supra). The construction of pCGN1557 is also described in co-pending U.S. application Ser. No. 07/494,722, filed Mar. 16, 1990.

EXAMPLE 5

Preparation of Transgenic Plants

This example describes the transformation of *Agrobacterium tumefaciens* with glycogen biosynthetic enzyme gene nucleic acid constructs in accordance with the present invention and the cocultivation of these *A. tumefaciens* with plant cells to produce transgenic plants containing the glycogen constructs.

A. Transformation of *Agrobacterium tumefaciens*

Cells of *Agrobacterium tumefaciens* strain 2760 (also known as LBA4404, Hoekema et al., *Nature* (1983) 303:179–180) are transformed with binary vectors, such as pCGN1457, pCGN1457B and pCGN1455 (as described in Example 4) using the method of Holsters, et al., *(Mol. Gen. Genet.*, (1978) 163:181–187). The transformed *A. tumefaciens* are then used in the co-cultivation of plants.

The Agrobacterium are grown on AB medium (K$_2$HPO$_4$6g/l, NaH$_2$PO$_4$.H$_2$O 2.3 g/l, NH$_4$Cl 2 g/l, KCl 3 g/l, glucose 5 g/l, FeSO$_4$ 2.5 mg/1, MgSO$_4$246 mg/1 , CaCl$_2$14.7 mg/1, 15 g/1 agar), plus 100 µg/l gentamycin sulfate and 100 µg/l streptomycin sulfate for 4–5 days. Single colonies are inoculated into 10 ml of MG/L broth (per liter: 5 g mannitol, 1 g L-Glutamic acid or 1.15 g sodium glutamate, 0.5 g KH$_2$PO$_4$, 0.10 g NaCl, 0.10 g MgSO$_4$.7H$_2$O, 1 µg biotin, 5 g tryptone, 2.5 g yeast extract; adjust pH to 7.0) and are incubated overnight in a shaker at 30° C. and 180rpm. Prior to co-cultivation, the Agrobacterium culture is centrifuged at 12,000×g for 10 minutes and resuspended in 20 ml of MS medium (#510-1118, Gibco; Grand Island, N.Y.).

B. Cocultivation with Potato Cells

Feeder plates are prepared by pipetting 0.5 ml of a tobacco suspension culture ($\sim 10^6$ cells/ml) onto 0.8 % agar co-cultivation medium, containing Murashige and Skoog salts (#510-117, Gibco; Grand Island, N.Y.), thiamine-HCl (1.0 mg/l), nicotinic acid (0.5 mg/l) , pyridoxine HCl (0.5 rag/l) , sucrose (30 g/l) , zeatin riboside (5 µM) , 3-indoleacetyl-DL-aspartic acid (3 µM), pH 5.9. The feeder plates are prepared one day in advance and incubated at 25° C. A sterile 3 mm filter paper disk is placed on top of the tobacco cells after the suspension cells have grown for one day.

Tubers of *Solanum tuberosum* var Russet Burbank between the age of 1 and 6 months post harvest are peeled and washed in distilled water. All subsequent steps are carried out in a flow hood using sterile techniques. For surface sterilization, tubers are immersed in a solution of 10% commercial bleach (sodium hypochlorite) with 2 drops of Ivory ® liquid soap per 100 ml for 10 minutes. Tubers are rinsed six times in sterile distilled water and kept immersed in sterile liquid MS medium (#1118, Gibco; Grand Island; N.Y.) to prevent browning.

Tuber discs (1-2 mm thick) are prepared by cutting columns of potato tuber with a $\sim 1$ cm in diameter cork borer and slicing the columns into discs of the desired thickness. Discs are placed into the liquid MS medium culture of the transformed Agrobacterium tumefaciens containing the binary vector of interest ($1 \times 10^7$-$1 \times 10^8$ bacteria/ml) until thoroughly wetted. Excess bacteria are removed by blotting discs on sterile paper towels. The discs are co-cultivated with the bacteria for 48 hours on the feeder plates and then transferred to regeneration medium (co-cultivation medium plus 500 mg/l carbenicillin and 100 mg/l kanamycin). In 3 to 4 weeks, shoots develop from the discs.

When shoots are approximately 1 cm, they are excised and transferred to a 0.8% agar rooting medium containing MS salts, thiamine-HCl (1.0 mg/l), nicotinic acid (0.5 Mg/l), pyridoxine-HCl (0.5 mg/l), sucrose (30 g/l), carbenicillin (200 mg/l) and kanamycin (100–200 mg/l) pH 5.9. Plants are rooted two times with at least one rooting taking place on rooting medium with the higher level of kanamycin (200 mg/l). Plants which have rooted twice are then confirmed as transformed by performing NPTII blot activity assays (Radke, S. E. et al, *Theor, Appl. Genet.* (1988) 75:685–694). Plants which are not positive for NPTII activity are discarded.

EXAMPLE 6

Analysis of Tubers from Transformed Potato Plants

In this Example, measurement of specific gravity in tubers from transgenic potato plants is described.

Rooted plants, transformed as described in Example 5, are cut into five sections at the internodes and each section is rooted again, also as described in Example 5. The newly rooted plants are transplanted from rooting medium to soil and placed in a growth chamber (21° C., 16 hour days with 250–300 µE/m$^2$/sec). Soil is prepared as follows: For about 340 gallons, combine 800 pounds 20/30 sand (approximately 14 cubic feet), 16 cubic feet Fisons Canadian Peat Moss, 16 cubic feet #3 vermiculite, and approximately 4.5 pounds hydrated lime in a Gleason mixer. The soil is steamed in the mixer for two hours; the mixer mixes for about 15 seconds at intervals of fifteen minutes over a period of one hour to ensure even heating throughout the soil. During and after the process of steaming, the soil reaches temperatures of at least 180° F. for one hour. The soil is left in the mixer until the next day. At that time, hydrated lime is added, if necessary, to adjust the pH to range between 6.30 and 6.80.

The relative humidity of the growth chamber is maintained at 70–90% for 2–4 days, after which the humidity is maintained at 40–60%. When plants are well established in the soil, after approximately two weeks, they are transferred to a greenhouse. In the greenhouse, plants are grown in 6.5 inch pots in a soil mix of peat:-perlite:vermiculite (11:1:9), at an average temperature of 24° C. day/12° C. night. Day length is approximately 12 hours and light intensity levels vary from approximately 600 to 1000 µE/m²/sec.

Tubers from each plant are harvested and washed 14 weeks after transfer to the greenhouse. Immediately after harvest, three to five uniformly sized tubers from each pot are weighed and their specific gravity determined. In determining specific gravity, the tubers from each plant are first collectively weighed in air and then collectively weighed in water. Specific gravity is determined, where x=the weight of tubers in air and y=the weight of tubers in water, as x/(x−y).

In general, the specific gravities of tubers from five replicates of plants transformed with the glgA constructs (pCGN1457 and pCGN1457B) and of tubers from control plants are determined. Control plants include regenerated non-transformed potato plants and transgenic potato plants which lack the glgA constructs. Controls are subjected to the transformation and regeneration culture and growth conditions described above in production of glgA transformed plants. To compare values from each tuber sample, the specific gravity measurements are converted to reflect % total solids content of tubers. Percent total solids is calculated as (specific gravity)×(199.63)−194.84 (Porter, et al., Am. Pot. J. (1964) 41:329–336). Differences are detected in percent total solids as determined for tubers from several of the glgA transformed plants as compared to tubers from control plants. Results are presented in Table 1 which represent average specific gravity of tubers of 5 replicate plants, except as otherwise indicated. Specific gravity measurements were determined for three to five uniformly sized tubers from each plant and the measurements of the tubers from the replicate plants were then averaged to determine average specific gravity (SpGr) of tubers for each transformation event. Values for one set of transformed control plants (Tx) and one set of untransformed/regenerated control plants (Rg) for each construct are shown at the top of their respective columns. Transformed control plants were transformed with a non-carbohydrate-related gene.

TABLE 1

| Average Specific Gravity Measurements | | | |
|---|---|---|---|
| Event | SpGr | Event | SpGr |
| Controls | | Controls | |
| Tx | 1.079 | Tx | 1.083 |
| Rg | 1.081 | *Rg | 1.077 |
| Transformed Plants | | Transformed Plants | |
| 1457-3 | 1.073 | 1457B-3 | 1.062 |
| 1457-4 | 1.060 | 1457B-4 | 1.075 |
| 1457-6 | 1.076 | 1457B-5 | 1.073 |
| 1457-7 | 1.080 | 1457B-7 | 1.066 |
| 1457-8 | 1.077 | 1457B-8 | 1.066 |
| 1457-9 | 1.067 | 1457B-9 | 1.063 |
| 1457-10 | 1.083 | 1457B-10 | 1.075 |
| 1457-11 | 1.065 | 1457B-12 | 1.065 |
| 1457-12 | 1.066 | 1457B-13 | 1.058 |
| 1457-13 | 1.080 | *1457B-15 | 1.053 |
| 1457-14 | 1.062 | 1457B-16 | 1.075 |
| 1457-15 | 1.064 | 1457B-17 | 1.053 |
| 1457-16 | 1.068 | 1457B-18 | 1.068 |
| 1457-17 | 1.069 | 1457B-21 | 1.081 |
| 1457-18 | 1.060 | 1457B-22 | 1.067 |
| 1457-19 | 1.069 | 1457B-23 | 1.069 |
| 1457-20 | 1.066 | 1457B-24 | 1.068 |
| 1457-22 | 1.068 | | |

*Only 4 replicate plants were available for these samples.

It is readily apparent from the data presented in Table 1 that transgenic plants were obtained which produce tubers having an altered specific gravity as compared to the tubers from control plants.

Statistical analysis was conducted on the specific gravity measurements of tubers from the 5 replicates of one of the transformation events as compared to the specific gravity measurements of tubers from two control events. The event analyzed was 1457-4 which had an average specific gravity of 1.060. The specific gravity measurements of tubers from the individual replicates that were used to calculate the average for this event were 1.059, 1.057, 1.067, 1.066, and 1.053. The specific gravity measurements for replicates of control tubers were as follows. Tx (ave. 1.079): 1.076, 1.082, 1.073, 1.083, and 1.079. Rg (ave. 1.081): 1.076, 1.087, 1.083, 1.082, and 1.077. These measurements were converted to percent solids as described above and the percent solids values were used for statistical analysis as follows.

A comparison of sample means was conducted on the percent solids values calculated for the three events, 1457-4, Tx and Rx, by calculating the t value (Student's t) and determining statistical difference based on a standard table of values for t. (See, for example, Steel and Tottie (1980) *Principles and Procedures of Statistics: A Biometrical Approach* (McGraw-Hill pub.) Chapter 5 and Table A.3). These analyses indicate a significant difference between the average specific gravity measurements of transgenic tubers as compared to control tubers at a confidence level of greater than 99%. The average specific gravity measurements of the two control groups were not significantly different.

Further analysis may be conducted on tubers from selected pCGN1457 and pCGN1457B transformed plants and from non-transformed controls (RB-43) to determine starch content, amylose percentages and to elucidate chain length distribution in the amylopectin component of the starch. Starch granules are isolated as described by Boyer et al. (1976) *Cereal Chemistry* 53:327–337) and starch content estimated on a weight basis (starch wt/fresh wt). Amylose percentages are determined by gel-filtration analysis (Boyer et al. (1985) *Starch/Starke* 37:73–79). Chain length distribution patterns are determined by HPLC analysis as described by Sanders et al. (1990) *Cereal Chemistry* 67:594–602). Amylopectins are characterized by the ratios (on a weight basis) of low molecular weight chains to high molecular weight chains as described by Hizukuri (*Carbohydrate Research* (1985) 141:295–306). Results of these analyses are presented in Table 2.

TABLE 2

| Analyses of Transgenic Potato Tuber Starch | | | | | | |
|---|---|---|---|---|---|---|
| Construct | Spec. Gravity | % Starch | % Amylose | % High M.W. Chains | % Low M.W. Chains | Low M.W./ High M.W. |
| RB-43 | 1.081 | 17.1 | 23 | 33 | 66 | 2.0 |
| 1457-4 | 1.060 | 11.0 | 12 | 20 | 80 | 4.0 |
| 1457-17 | 1.069 | 14.6 | 24 | 28 | 72 | 2.6 |
| 1457-18 | 1.060 | 11.8 | 8 | 15 | 85 | 5.7 |
| RB-43 | 1.077 | 17.2 | 27 | | | |
| 1457B-15 | 1.053 | 9.0 | 9 | 15 | 85 | 5.7 |
| 1457B-17 | 1.053 | 12.5 | 19 | 26 | 84 | 3.2 |

The data presented in Table 2 indicate that tubers from transgenic plants which have an altered specific gravity, also have altered starch. In particular, the percentage of amylose in the transgenic potato tubers is decreased. In addition, the amylopectin portion of the starch from transgenic potato tubers has more low molecular weight chains and less high molecular weight chains than wild type potato tuber amylopectin, thus indicating that the amylopectin from transgenic tubers has more branch points.

It is evident from the above results, that plant cells and plants can be produced which have improved properties or may produce a desired product. In accordance with the subject invention, it is now seen that glycogen biosynthesis enzyme sequences may be introduced into a plant host cell and be used to express such enzyme or enzymes or to modify native starch precursors. Moreover, it is seen that such enzymes demonstrate biological activity on plant starch precursors resulting in a demonstrable phenotype in planta, namely altered specific gravity. In addition, the activity of glycogen biosynthetic enzymes in plants has been shown to result in starch having altered properties, in particular altered ratios of amylose/amylopectin and altered distribution of low molecular weight chain lengths to high molecular weight chain lengths in the amylopectin fraction. In this manner, plants, including plant cells and plant parts, having modified starch properties may be obtained, wherein the modified starch has unique and desirous properties.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teaching of this invention that certain changes and modifications may be made thereto without departing from the spirit or scope of the appended claims.

What is claimed is:

1. A nucleic acid construct comprising the encoding sequence from an *E. coli* glgA gene and a plant plastid transit peptide encoding sequence.

2. The construct of claim 1 wherein said glgA gene is from *E. coli* strain 618.

3. The construct of claim 1 comprising in the 5'-3' direction of transcription, a transcription initiation region, a translational initiation region, said plastid transit peptide encoding sequence, said *E. coli* glgA encoding sequence, and a transcription/translational termination region, wherein said transcription initiation region is capable of functioning in a plant cell.

4. The construct of claim 3 wherein said transcription initiation region comprises the regulatory region 5' to a patatin gene from *Solanum tuberosum*.

5. The construct of claim 3 further comprising a T-DNA border.

6. A plant cell comprising *E. coli* glycogen synthase.

7. The plant cell of claim 6 wherein said enzyme is present in an amyloplast.

8. The plant cell of claim 6 wherein said plant is selected from the group consisting of corn, sorghum, rice, potato, tapioca, cassava, arrowroot, and sago.

9. The plant cell of claim 6, wherein said plant is a cereal grain plant.

10. A plant comprising a cell of any one of claims 6, 7, 8, or 9.

11. A method to modify a potato tuber, wherein said method comprises
growing a potato plant, under conditions that will permit the formation of a potato tuber, wherein the genome of said potato plant comprises a construct according to claim 3, and wherein said transcription initiation region is from a patatin gene.

12. The method of claim 11 wherein expression of said *E. coli* glycogen synthase results in modification of the starch composition of said potato tuber.

13. The method of claim 12 wherein said modified starch has an altered amylose to amylopectin ratio as compared to that of a control starch storage organ.

14. The method of claim 11 wherein said potato tuber comprises modified starch having an altered ratio of low to high molecular weight chains in the amylopectin fraction of said starch, as compared to that of a control potato tuber.

15. A potato tuber having modified starch, wherein said starch modification consists of an increased percentage of low molecular weight chains in the amylopectin portion of said starch, and wherein said potato tuber is produced according to the method of claim 11.

16. The potato tuber of claim 15, wherein the amylopectin fraction of the starch in said potato tuber has a ratio of low to high molecular weight chains of at least 4.0.

* * * * *

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 1464 base pairs
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO: 1:

```
GATCTAACAG  GAGCGATAAT  GCAGGTTTTA  CATGTATGTT  CAGAGATGTT  CCCGCTGCTT    60
AAAACCGGCG  GTCTGGCTGA  TGTTATTGGG  GCATTACCCG  CAGCACAAAT  CGCAGACGGC   120
GTTGACGCTC  GCGTACTGTT  GCCTGCATTT  CCCGATATTC  GCCGTGGCGT  GACCGATGCG   180
CAGGTAGTAT  CCCGTCGTGA  TACCTTCGCC  GGACATATCA  CGCTGTTGTT  CGGTCATTAC   240
AACGGGGTTG  GCATTTACCT  GATTGACGCG  CCGCATCTCT  ATGATCGTCC  GGGAAGCCCG   300
TATCACGATA  CCAACTTATT  TGCCTATACC  GACAACGTAT  GCGTTTTGC   GCTGCTGGGG   360
TGGGTTGGGG  CAGAAATGGC  CAGCGGGCTT  GACCCATTCT  GGCGTCCTGA  TGTGGTGCAT   420
GCGCACGACT  GGCATGCAGG  CCTTGCGCCT  GCGTATCTGG  CGGCGCGCGG  GCGTCCGGCG   480
AAGTCGGTGT  TTACTGGGCA  CAACCTGGCC  TATCAAGGCA  TGTTTATGC   ACATCACATG   540
AATGACATCC  AATTGCCATG  GTCATTCTTT  AATATTCATG  GGCTGGAATT  CAACGGACAA   600
ATCTCTTTCC  TGAAGGCCGG  TCTGTACTAT  GCCGATCACA  TTACGGCGGT  CAGTCCAACC   660
TACGCTCGCG  AGATCACCGA  ACCGCAGTTT  GCCTACGGTA  TGGAAGGTCT  GTTGCAACAG   720
CGTCACCGTG  AAGGGCGTCT  TTCCGGCGTA  CTGAACGGCG  TGGACGAGAA  AATCTGGAGT   780
CCAGAGACGG  ACTTACTGTT  GGCCTCGCGT  TACACCCGCG  ATACGTTGGA  AGATAAAGCG   840
GAAAATAAGC  GCCAGTTACA  AATCGCAATG  GGGCTTAAGG  TTGACGATAA  AGTGCCGCTT   900
TTTGCAGTGG  TGAGCCGTCT  GACCAGCCAG  AAAGGTCTCG  ACCTGGTGCT  GGAAGCCTTA   960
CCGGGTCTTC  TGGAGCAGGG  CGGGCAGCTG  GCGCTACTCG  GCGCGGGCGA  TCCGGTGCTG  1020
CAGGAAGGTT  TCCTTGCGGC  GGCAGCGGAA  TACCCCGGTC  AGGTGGGCGT  TCAGATTGGC  1080
TATCACGAAG  CATTTTCGCA  TCGCATTATG  GGCGGCGCGG  ACGTCATTCT  GGTGCCCAGC  1140
CGTTTTGAAC  CGTGCGGCTT  AACGCAACTT  TATGGATTGA  AGTACGGTAC  GCTGCCGTTA  1200
```

```
GTGCGGCGCA CCGGTGGGCT TGCTGATACG GTTTCTGACT GTTCTCTTGA GAACCTTGCA    1260

GATGGCGTCG CCAGTGGGTT TGTCTTTGAA GATAGTAATG CCTGGTCGCT GTTACGGGCT    1320

ATTCGACGTG CTTTTGTACT GTGGTCCCGT CCTTCACTGT GGCGGTTTGT GCAACGTCAG    1380

GCTATGGCAA TGGATTTTAG CTGGCAGGTC GCGGCGAAGT CGTACCGTGA GCTTTACTAT    1440

CGCTCGAAAT AGTTTTCAGT CGAC                                           1464
```

( 2 ) INFORMATION FOR SEQ ID NO: 2:

( i ) SEQUENCE CHARACTERISTICS:
        ( A ) LENGTH: 477 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 2:

```
Met Gln Val Leu His Val Cys Ser Glu Met Phe Pro Leu Leu Lys Thr
 1               5                  10                  15

Gly Gly Leu Ala Asp Val Ile Gly Ala Leu Pro Ala Ala Gln Ile Ala
                20                  25                  30

Asp Gly Val Asp Ala Arg Val Leu Leu Pro Ala Phe Pro Asp Ile Arg
                35                  40                  45

Arg Gly Val Thr Asp Ala Gln Val Val Ser Arg Arg Asp Thr Phe Ala
                50                  55                  60

Gly His Ile Thr Leu Leu Phe Gly His Tyr Asn Gly Val Gly Ile Tyr
 65                  70                  75                  80

Leu Ile Asp Ala Pro His Leu Tyr Asp Arg Pro Gly Ser Pro Tyr His
                85                  90                  95

Asp Thr Asn Leu Phe Ala Tyr Thr Asp Asn Val Leu Arg Phe Ala Leu
                100                 105                 110

Leu Gly Trp Val Gly Ala Glu Met Ala Ser Gly Leu Asp Pro Phe Trp
                115                 120                 125

Arg Pro Asp Val Val His Ala His Asp Trp His Ala Gly Leu Ala Pro
    130                 135                 140

Ala Tyr Leu Ala Ala Arg Gly Arg Pro Ala Lys Ser Val Phe Thr Gly
145                 150                 155                 160

His Asn Leu Ala Tyr Gln Gly Met Phe Tyr Ala His His Met Asn Asp
                165                 170                 175

Ile Gln Leu Pro Trp Ser Phe Phe Asn Ile His Gly Leu Glu Phe Asn
                180                 185                 190

Gly Gln Ile Ser Phe Leu Lys Ala Gly Leu Tyr Tyr Ala Asp His Ile
                195                 200                 205

Thr Ala Val Ser Pro Thr Tyr Ala Arg Glu Ile Thr Glu Pro Gln Phe
    210                 215                 220

Ala Tyr Gly Met Glu Gly Leu Leu Gln Gln Arg His Arg Glu Gly Arg
225                 230                 235                 240

Leu Ser Gly Val Leu Asn Gly Val Asp Glu Lys Ile Trp Ser Pro Glu
                245                 250                 255

Thr Asp Leu Leu Leu Ala Ser Arg Tyr Thr Arg Asp Thr Leu Glu Asp
                260                 265                 270

Lys Ala Glu Asn Lys Arg Gln Leu Gln Ile Ala Met Gly Leu Lys Val
                275                 280                 285

Asp Asp Lys Val Pro Leu Phe Ala Val Val Ser Arg Leu Thr Ser Gln
    290                 295                 300

Lys Gly Leu Asp Leu Val Leu Glu Ala Leu Pro Gly Leu Leu Glu Gln
305                 310                 315                 320
```

```
Gly Gly Gln Leu Ala Leu Leu Gly Ala Gly Asp Pro Val Leu Gln Glu
            325             330                 335
Gly Phe Leu Ala Ala Ala Ala Glu Tyr Pro Gly Gln Val Gly Val Gln
            340             345                 350
Ile Gly Tyr His Glu Ala Phe Ser His Arg Ile Met Gly Gly Ala Asp
        355                 360             365
Val Ile Leu Val Pro Ser Arg Phe Glu Pro Cys Gly Leu Thr Gln Leu
    370             375             380
Tyr Gly Leu Lys Tyr Gly Thr Leu Pro Leu Val Arg Arg Thr Gly Gly
385             390             395                         400
Leu Ala Asp Thr Val Ser Asp Cys Ser Leu Glu Asn Leu Ala Asp Gly
            405             410                 415
Val Ala Ser Gly Phe Val Phe Glu Asp Ser Asn Ala Trp Ser Leu Leu
        420             425             430
Arg Ala Ile Arg Arg Ala Phe Val Leu Trp Ser Arg Pro Ser Leu Trp
        435             440             445
Arg Phe Val Gln Arg Gln Ala Met Ala Met Asp Phe Ser Trp Gln Val
    450             455             460
Ala Ala Lys Ser Tyr Arg Glu Leu Tyr Tyr Arg Ser Lys
465             470             475
```

(2) INFORMATION FOR SEQ ID NO: 3:

(i) SEQUENCE CHARACTERISTICS:
        (A) LENGTH: 1323 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO: 3:

```
GATCTAGGAG CGATA ATG GTT AGT TTA GAG AAG AAC GAT CAC TTA ATG            48
                 Met Val Ser Leu Glu Lys Asn Asp His Leu Met
                  1               5                   10

TTG GCG CGC CAG CTG CCA TTG AAA TCT GTT GCC CTG ATA CTG GCG GGA         96
Leu Ala Arg Gln Leu Pro Leu Lys Ser Val Ala Leu Ile Leu Ala Gly
            15                  20                  25

GGA CGT GGT ACC CGC CTG AAG GAT TTA ACC AAT AAG CGA GCA AAA CCG        144
Gly Arg Gly Thr Arg Leu Lys Asp Leu Thr Asn Lys Arg Ala Lys Pro
        30                  35                  40

GCC GTA CAC TTC GGC GGT AAG TTC CGC ATT ATC GAC TTT GCG CTG TCT        192
Ala Val His Phe Gly Gly Lys Phe Arg Ile Ile Asp Phe Ala Leu Ser
    45                  50                  55

AAC TGC ATC AAC TCC GGG ATC CGT CGT ATG GGC GTG ATC ACC CAG TAC        240
Asn Cys Ile Asn Ser Gly Ile Arg Arg Met Gly Val Ile Thr Gln Tyr
60                  65                  70                  75

CAG TCC CAC ACT CTG GTG CAG CAC ATT CAG CGC GGC TGG TCA TTC TTC        288
Gln Ser His Thr Leu Val Gln His Ile Gln Arg Gly Trp Ser Phe Phe
                80                  85                  90

AAT GAA GAA ATG AAC GAG TTT GTC GAT CTG CTG CCA GCA CAG CAG AGA        336
Asn Glu Glu Met Asn Glu Phe Val Asp Leu Leu Pro Ala Gln Gln Arg
            95                  100                 105

ATG AAA GGG GAA AAC TGG TAT CGC GGC ACC GCA GAT GCG GTC ACC CAA        384
Met Lys Gly Glu Asn Trp Tyr Arg Gly Thr Ala Asp Ala Val Thr Gln
        110                 115                 120

AAC CTC GAC ATT ATC CGC CGT TAT AAA GCG GAA TAC GTG GTG ATC CTG        432
Asn Leu Asp Ile Ile Arg Arg Tyr Lys Ala Glu Tyr Val Val Ile Leu
    125                 130                 135

GCG GGC GAC CAT ATC TAC AAG CAA GAC TAC TCG CGT ATG CTT ATC GAT        480
```

| | | | | | | | | | | | | | | | | |
|---|---|---|---|---|---|---|---|---|---|---|---|---|---|---|---|---|
| Ala | Gly | Asp | His | Ile | Tyr | Lys | Gln | Asp | Tyr | Ser | Arg | Met | Leu | Ile | Asp | |
| 140 | | | | 145 | | | | | 150 | | | | | | 155 | |

| CAC | GTC | GAA | AAA | GGC | GCA | CGT | TGC | ACC | GTT | GCT | TGT | ATG | CCA | GTA | CCG | 528 |
|---|---|---|---|---|---|---|---|---|---|---|---|---|---|---|---|---|
| His | Val | Glu | Lys | Gly | Ala | Arg | Cys | Thr | Val | Ala | Cys | Met | Pro | Val | Pro | |
| | | | 160 | | | | | 165 | | | | | | 170 | | |

| ATT | GAA | GAA | GCC | TCC | GCA | TTT | GGC | GTT | ATG | GCG | GTT | GAT | GAG | AAC | GAT | 576 |
|---|---|---|---|---|---|---|---|---|---|---|---|---|---|---|---|---|
| Ile | Glu | Glu | Ala | Ser | Ala | Phe | Gly | Val | Met | Ala | Val | Asp | Glu | Asn | Asp | |
| | | | 175 | | | | | 180 | | | | | | 185 | | |

| AAA | ATT | ATC | GAA | TTC | GTT | GAA | AAA | CCT | GCT | AAC | CCG | CCG | TCA | ATG | CCG | 624 |
|---|---|---|---|---|---|---|---|---|---|---|---|---|---|---|---|---|
| Lys | Ile | Ile | Glu | Phe | Val | Glu | Lys | Pro | Ala | Asn | Pro | Pro | Ser | Met | Pro | |
| | | 190 | | | | | 195 | | | | | 200 | | | | |

| AAC | GAT | CCG | AGC | AAA | TCT | CTG | GCG | AGT | ATG | GGT | ATC | TAC | GTC | TTT | GAC | 672 |
|---|---|---|---|---|---|---|---|---|---|---|---|---|---|---|---|---|
| Asn | Asp | Pro | Ser | Lys | Ser | Leu | Ala | Ser | Met | Gly | Ile | Tyr | Val | Phe | Asp | |
| | 205 | | | | | 210 | | | | | 215 | | | | | |

| GCC | GAC | TAT | CTG | TAT | GAA | CTG | CTG | GAA | GAA | GAC | GAT | CGC | GAT | GAG | AAC | 720 |
|---|---|---|---|---|---|---|---|---|---|---|---|---|---|---|---|---|
| Ala | Asp | Tyr | Leu | Tyr | Glu | Leu | Leu | Glu | Glu | Asp | Asp | Arg | Asp | Glu | Asn | |
| 220 | | | | | 225 | | | | | 230 | | | | | 235 | |

| TCC | AGC | CAC | GAC | TTT | GGC | AAA | GAT | TTG | ATT | CCC | AAG | ATC | ACC | GAA | GCC | 768 |
|---|---|---|---|---|---|---|---|---|---|---|---|---|---|---|---|---|
| Ser | Ser | His | Asp | Phe | Gly | Lys | Asp | Leu | Ile | Pro | Lys | Ile | Thr | Glu | Ala | |
| | | | | 240 | | | | | 245 | | | | | 250 | | |

| GGT | CTG | GCC | TAT | GCG | CAC | CCG | TTC | CCG | CTC | TCT | TGC | GTA | CAA | TCC | GAC | 816 |
|---|---|---|---|---|---|---|---|---|---|---|---|---|---|---|---|---|
| Gly | Leu | Ala | Tyr | Ala | His | Pro | Phe | Pro | Leu | Ser | Cys | Val | Gln | Ser | Asp | |
| | | | 255 | | | | | 260 | | | | | 265 | | | |

| CCG | GAT | GCC | GAG | CCG | TAC | TGG | CGC | GAT | GTG | GGT | ACG | CTG | GAA | GCT | TAC | 864 |
|---|---|---|---|---|---|---|---|---|---|---|---|---|---|---|---|---|
| Pro | Asp | Ala | Glu | Pro | Tyr | Trp | Arg | Asp | Val | Gly | Thr | Leu | Glu | Ala | Tyr | |
| | | 270 | | | | | 275 | | | | | 280 | | | | |

| TGG | AAA | GCG | AAC | CTC | GAT | CTG | GCC | TCT | GTG | GTG | CCG | GAA | CTG | GAT | ATG | 912 |
|---|---|---|---|---|---|---|---|---|---|---|---|---|---|---|---|---|
| Trp | Lys | Ala | Asn | Leu | Asp | Leu | Ala | Ser | Val | Val | Pro | Glu | Leu | Asp | Met | |
| | 285 | | | | | 290 | | | | | 295 | | | | | |

| TAC | GAT | CGC | AAT | TGG | CCA | ATT | CGC | ACC | TAC | AAT | GAA | TCA | TTA | CCG | CCA | 960 |
|---|---|---|---|---|---|---|---|---|---|---|---|---|---|---|---|---|
| Tyr | Asp | Arg | Asn | Trp | Pro | Ile | Arg | Thr | Tyr | Asn | Glu | Ser | Leu | Pro | Pro | |
| 300 | | | | | 305 | | | | | 310 | | | | | 315 | |

| GCG | AAA | TTC | GTG | CAG | GAT | CGC | TCC | GGT | AGC | CAC | GGG | ATG | ACC | CTT | AAC | 1008 |
|---|---|---|---|---|---|---|---|---|---|---|---|---|---|---|---|---|
| Ala | Lys | Phe | Val | Gln | Asp | Arg | Ser | Gly | Ser | His | Gly | Met | Thr | Leu | Asn | |
| | | | | 320 | | | | | 325 | | | | | 330 | | |

| TCA | CTG | GTT | TCC | GAC | GGT | TGT | GTG | ATC | TCC | GGT | TCG | GTG | GTG | GTG | CAG | 1056 |
|---|---|---|---|---|---|---|---|---|---|---|---|---|---|---|---|---|
| Ser | Leu | Val | Ser | Asp | Gly | Cys | Val | Ile | Ser | Gly | Ser | Val | Val | Val | Gln | |
| | | | 335 | | | | | 340 | | | | | 345 | | | |

| TCC | GTT | CTG | TTC | TCG | CGC | GTT | CGC | GTG | AAT | TCA | TTC | TGC | GAC | ATT | GAT | 1104 |
|---|---|---|---|---|---|---|---|---|---|---|---|---|---|---|---|---|
| Ser | Val | Leu | Phe | Ser | Arg | Val | Arg | Val | Asn | Ser | Phe | Cys | Asp | Ile | Asp | |
| | | 350 | | | | | 355 | | | | | 360 | | | | |

| TCC | GCC | GTA | TTG | TTA | CCG | GAA | GTA | TGG | GTA | GGT | CGC | TCG | TGC | CGT | CTG | 1152 |
|---|---|---|---|---|---|---|---|---|---|---|---|---|---|---|---|---|
| Ser | Ala | Val | Leu | Leu | Pro | Glu | Val | Trp | Val | Gly | Arg | Ser | Cys | Arg | Leu | |
| | 365 | | | | | 370 | | | | | 375 | | | | | |

| CGC | CGC | TGC | GTC | ATC | GAT | CGT | GCT | TGT | GTT | ATT | CCG | GAA | GGC | ATG | GTG | 1200 |
|---|---|---|---|---|---|---|---|---|---|---|---|---|---|---|---|---|
| Arg | Arg | Cys | Val | Ile | Asp | Arg | Ala | Cys | Val | Ile | Pro | Glu | Gly | Met | Val | |
| 380 | | | | | 385 | | | | | 390 | | | | | 395 | |

| ATT | GGT | GAA | AAC | GCA | GAG | GAA | GAT | GCA | CGT | CGT | TTC | TAT | CGT | TCA | GAA | 1248 |
|---|---|---|---|---|---|---|---|---|---|---|---|---|---|---|---|---|
| Ile | Gly | Glu | Asn | Ala | Glu | Glu | Asp | Ala | Arg | Arg | Phe | Tyr | Arg | Ser | Glu | |
| | | | | 400 | | | | | 405 | | | | | 410 | | |

| GAA | GGC | ATC | GTG | CTG | GTA | ACG | CGC | GAA | ATG | CTA | CGG | AAG | TTA | GGG | CAT | 1296 |
|---|---|---|---|---|---|---|---|---|---|---|---|---|---|---|---|---|
| Glu | Gly | Ile | Val | Leu | Val | Thr | Arg | Glu | Met | Leu | Arg | Lys | Leu | Gly | His | |
| | | | 415 | | | | | 420 | | | | | 425 | | | |

| AAA | CAG | GAG | CGA | TAATGCAGGG | TCGAC | 1323 |
|---|---|---|---|---|---|---|
| Lys | Gln | Glu | Arg | | | |
| | | | 430 | | | |

( 2 ) INFORMATION FOR SEQ ID NO: 4:

( i ) SEQUENCE CHARACTERISTICS:
        ( A ) LENGTH: 5 amino acids
        ( B ) TYPE: amino acid
        ( D ) TOPOLOGY: linear (i i) MOLECULE TYPE: peptide (x i) SEQUENCE DESCRIPTION: SEQ ID NO: 4:

Phe Glu Thr Leu Ser
1               5

(2) INFORMATION FOR SEQ ID NO: 5:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (i i) MOLECULE TYPE: other nucleic acid
        (A) DESCRIPTION: synthetic oligonucleotide (x i) SEQUENCE DESCRIPTION: SEQ ID NO: 5:

```
CAGGAGATCT TATTTTTACA ACAATTACCA ACAACAACAA ACAACAAACA ACATTACAAT    60
TACTATTTAC AATTACACCA TGGATCCGTC GACGAGCTC                            99
```